(12) United States Patent
Dakshanamurthy et al.

(10) Patent No.: US 10,916,331 B2
(45) Date of Patent: Feb. 9, 2021

(54) PREDICTING DRUG-TARGET INTERACTIONS AND USES FOR DRUG REPOSITIONING AND REPURPOSING

(71) Applicant: GEORGETOWN UNIVERSITY, Washington, DC (US)

(72) Inventors: Sivanesan Dakshanamurthy, Herndon, VA (US); Stephen W. Byers, Takoma Park, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 316 days.

(21) Appl. No.: 15/577,719

(22) PCT Filed: Jun. 3, 2016

(86) PCT No.: PCT/US2016/035639
§ 371 (c)(1),
(2) Date: Nov. 28, 2017

(87) PCT Pub. No.: WO2016/200681
PCT Pub. Date: Dec. 15, 2016

(65) Prior Publication Data
US 2018/0157786 A1    Jun. 7, 2018

Related U.S. Application Data

(60) Provisional application No. 62/172,639, filed on Jun. 8, 2015.

(51) Int. Cl.
*G16B 15/00* (2019.01)
*G16B 15/30* (2019.01)
(Continued)

(52) U.S. Cl.
CPC .............. *G16B 15/00* (2019.02); *G06F 5/01* (2013.01); *G06F 17/11* (2013.01); *G16B 15/30* (2019.02); *G06F 2111/10* (2020.01)

(58) Field of Classification Search
CPC ........ G06F 17/11; G06F 2217/16; G06F 5/01; G16B 15/00; G16B 15/30
See application file for complete search history.

(56) References Cited

U.S. PATENT DOCUMENTS 6,970,790 B2    11/2005  Kita et al.
8,703,438 B2 *  4/2014  Huang ..................... C12Q 1/37
                                                  435/23

(Continued)

FOREIGN PATENT DOCUMENTS

EP           1757943           10/2010
WO    WO 2013192573 A1 *       12/2013

OTHER PUBLICATIONS

The Author(s), "Activities at the Universal Protein Resource (Uniprot)", The UniProt Consortium, Nucleic Acids Research, vol. 42, 2014, pp. D191-D190.

(Continued)

*Primary Examiner* — Rehana Perveen
*Assistant Examiner* — Chuen-Meei Gan
(74) *Attorney, Agent, or Firm* — Kilpatrick Townsend & Stockton LLP

(57) ABSTRACT

Described herein are methods of predicting drug-target interactions and methods of using the information for drug repurposing. The methods described herein combine different descriptors, including, for example, atom pair similarity, shape, topology and chemical signatures, physico-chemical functional descriptors, contact points of the ligand and the target protein, chemical similarity, and docking score.

17 Claims, 10 Drawing Sheets

(51) Int. Cl.
G06F 5/01 (2006.01)
G06F 17/11 (2006.01)
G06F 111/10 (2020.01)

(56) References Cited

U.S. PATENT DOCUMENTS

2014/0206091 A1 7/2014 Gunawardena et al.
2015/0324546 A1* 11/2015 Dakshanamurthy ........................
G06F 19/3456
705/2

OTHER PUBLICATIONS

"OMIM, Online Mendelian Inheritance in Man", Available online at: http://omim.org/, 2014, 2pages.
Ackerstaff et al., "Anti-Inflammatory Agent Indomethacin Reduces Invasion and Alters Metabolism in Human Breast Cancer Cell Line", Neoplasia, vol. 9, No. 3, 2007, pp. 222-235.
Albers et al., "Ximelaganan Vs Warfarin for Stroke Prevention in Patients With Nonvalvular Atrial Fibrillation: A Randomized Trial", JAMA, vol. 293, No. 6, Feb. 9, 2005, pp. 690-698.
Al-Maawali et al., "Prenatal Growth Restiction, Retinal Dystrophy Diabetes Insepidus and White Matter Disease: Expanding the Spectrum of PRPS1-related Disorders", European Journal of Human Genetics, vol. 23, 2014, pp. 310-316.
Ashburn et al., "Drug Repositioning: Identifying and Developing New Uses for Existing Drugs", Nature Reviews, Drug Discovery, vol. 3. Aug. 2004, pp. 673-683.
Ashburner et al., "Gene Ontology: Tool for the Unification of Biology", The Gene Ontology Consortium Nat Genet, vol. 25, No. 1, May 2000, pp. 25-29.
Bai et al., "Antiparasitic Mebendazole Shows Survival Benefit in 2 Preclinical Models of Glioblastoma Multiforme", Neuro-Oncology, vol. 13, No. 9, 2011, pp. 974-982.
Barrett-Connor et al., "Effects of Raloxifene on Cardiovascular Events and Breast Cancer in Postmenopausal Women", The New England Journal Medicine, vol. 355, No. 2, Jul. 13, 2006, pp. 125-137.
Bohari et al., "FDA Approved Drugs Complexed to Their Targets: Evaluating Pose Prediction Accuracy for Docking Protocols", J. Mol. Model, vol. 18, 2012, pp. 4263-4274.
Bolton et al., "PubChem3D: A New Resource for Scientists", Journal of Cheminformatics, vol. 3, No. 32, 2011, 15 pages.
Broccatelli et al., "Best of Both Worlds: On the Complementarity of Ligand-Based and Structure-Based Virtual Screening", Journal of Chemical Information and Modeling, vol. 54, May 30, 2014, pp. 1634-1641.
Brosnan et al., "Orotic Acid Excretion and Arginine Metaboloism", The Journal of Nutrition, vol. 137, 2007, pp. 1656S-1661S.
Cai et al., "Peptide Deformylase is a Potential Target for Anti-Helicobacter Pylori Drugs: Reverse Docking, Enzymatic Assay, and X-ray Crystallography Validation", Protein Science, vol. 15, 2006, pp. 2071-2081.
Campillos et al., "Drug Target Identification Using Side-Effect Similarity", Science, vol. 321, Jul. 11, 2008, pp. 263-266.
Cano et al., "Selective Estrogen Receptor Modulators and Risk for Coronary Heart Disease", Climacteric, vol. 10, 2007, pp. 97-111.
Carbon et al., "AmiGo: Online Access to Ontology and Annotation Data", Bioinformatics, vol. 25, No. 2, 2009, pp. 288-289.
Carhart et al., "Atom Pairs as Molecular Features in Structure-Activity Studies: Definition and Applications", J. Chem. Inf. Comput. Sci., vol. 25, 1985, pp. 64-73.
Chen et al., "Assessing Drug Target Assocation Using Semantic Linked Data", PLoS Computational Biology, vol. 8, No. 7, e1002574, Jul. 2012, 10 pages.
Chen et al., "Ligand-Protein Inverse Docking and its Potential Use in the Computer Search of Protein Targets of a Small Molecules", Proteins, vol. 43, 2001, pp. 217-226.

Cheng et al., "Efficacy and Safety of Sorafenib in Patients in the Asia-pacific Region With Advanced Hepatocellular Carcinoma: A Phase III Randomised, Double-blind, Placebo-Controlled Trial", Lancet Oncol., vol. 10. 2009, pp. 25-34.
Cheng et al., "Prediction of Drug-Target Interactions and Drug Repositioning Via Network-Based Inference", PLoS Computational Biology, vol. 8, issue 5, e1002503, May 2012, 12 pages.
Choueiri et al., "Efficacy of Sunitinib and Sorafenib in Metastatic Papillary and Chromophobe Renal Cell Carcinoma", Journal of Clinical Oncology, vol. 26, No. 1, Jan. 1, 2008, pp. 127-131.
Corbin et al., "Diencephalic Involvement in Generaliized Lipodystrophy: Rationale and Treatment With the Neuroleptic Agent, Pimozide", Acta. Endocrinol (Copenh), vol. 77, 1974, pp. 209-220.
Cunningham et al., "Effects of the Calcimimetic Cinacalcet Hcl on Cardiovascular Disease, Fracture, and Health-related Quality of Life in Secondary Hyperparathyroidism", Kidney International, vol. 68, 2005, pp. 1793-1800.
Curtin et al., "Psychological Stress Suppresses Innate IFN-Gamma Production via Glucocorticoid Receptor Activation: Reversal by the Aniolytic Chlordiazepoxide", Brain, Behav. Immun., vol. 23, 2009, pp. 535-547.
Dakshanamurthy et al., "Predicting New Indications for Approved Drugs Using a Proteochemometric Method", J. Med. Chem., vol. 55, Aug. 9, 2012, pp. 6832-6848.
Danquah et al., "Micellar Delivery of Bicalutamide and Embelin for Treating Prostrate Cancer", Pharm. Res., vol. 26, 2009, pp. 2081-2092.
Das et al., "Rapid Comparison of Protein Binding Site Surfaces with Property Encoded Shape Distributions (PESD)", J. Chem. Inf. Model, vol. 49, No. 12, Dec. 2009, pp. 2863-2872.
Davis et al., "The Comparative Toxicgenomics Database: Update 2013", Nucleic Acids Research, vol. 41, 2013, pp. D1104-D1114.
De Franchi et al., "Binding of Protein Kinase Inhibitors to Synapsin I Inferred From Pair-Wise Binding Site Similarity Measurements", PLoS One, vol. 5, Issue 8, e12214, Aug. 2010, 11 pages.
De Lavallade et al., "Pleural Effusions in Patients With Chronic Myeloid Leukaemia Treated With Dasatinib May Have an Immune-Mediated Pathogenesis", British Journal Haematology, vol. 141, 2008, pp. 745-747.
Dennerstein et al., "Menstrual Migraine: A Double-Blind Trial of Percutaneous Estradiol", Gynecol Endocrinol, vol. 2, 1988, pp. 113-120.
Do et al., "The Example of Epsilon-Viniferin", Curr. Drug. Discov. Technol., vol. 2, 2005, pp. 161-167.
Dobrosotskaya et al., "Mebendazole Monotherapy and Long-Term Disease Control in Metastatic Adrenocortical Carcinoma", Endocr. Pract., vol. 17, 2011, pp. e59-e62.
Doudican et al., "Mebendazole Induces Apoptosis via Bcl-2 Inactivation in Chemoresistant Melanoma Cells", Molecular Cancer Research, vol. 6, No. 8, Aug. 2008, pp. 1308-1315.
Doudican et al., "XIAP Downregulation Accompanies Mebendazole Growth Inhibition in Melanoma Xenografts", Anticancer Drugs, vol. 24, 2013, pp. 181-188.
Drazen et al., "Ezetimibe and Cancer—An Uncertain Association", N Engl J Med, vol. 359, No. 13, Sep. 25, 2008, pp. 1398-1399.
Eckle et al., "Immunohistochemical Detection of Activated Caspases in Apoptotic Hepatocytes in Rat Liver", Toxicologic Pathology, vol. 32, No. 1, 2004, pp. 9-15.
Eisen et al., "Sorafenib in Advanced Melanoma: A Phase II Randomised Discontinuation Trial Analysis", British Journal of Cancer, vol. 95, 2006, pp. 581-586.
Fabian et al., "A small Molecule-Kinase Interaction Map for Clinical Kinase Inhibitors", Nat. Biotechnol., vol. 23, 2005, pp. 329-336.
Franceschini et al., "String v9.1: Protein-protein Interaction Networks, With Increased Coverage and Integration", Nucleic Acids Research, vol. 41, 2013, pp. D808-D815.
Goh et al., "The Human Disease Network", PNAS, vol. 104, No. 21, May 22, 2007, pp. 8685-8690.
Goldenberg et al., "Use of Cyproterone Acetate in Prostate Cancer", Urol. Clin. North Am., vol. 18, 1991, pp. 111-122.
Green et al., "Altered Cognitive Function in Men Treated for Prostate Cancer With Luteinizing Hormone-Releasing Hormone

(56) References Cited

OTHER PUBLICATIONS

Analogues and Cyproterone Acetate: A Randomized Controlled Trial", BJU International, vol. 90, 2002, pp. 427-432.
Griffin et al., "The Influence of Pharmacogenetics on Fatty Liver Disease in the Wislar and Kyoto Rats: A Combined Transcriptomic and Metonomic Study", J. Proteome. Research, vol. 6, 2007, pp. 54-61.
Grover-Paez et al., "Raloxifene Modifies the Insulin Sensitivity and Lipid Profile of Postmenopausal Insulin Resistant Women", Gynecol Endocrinol, vol. 29, 2013, pp. 674-677.
Harris et al., "Nonsteroidal Antiinflammatory Drugs and Breast Cancer", Epidemiology, vol. 7, 1996. pp. 203-205.
Haupt et al., "Old Friends in New Guise: Repositioning of Known Drugs with Structural Bioinformatics", Briefings in Bioinformatics, vol. 12, No. 4, Mar. 26, 2011, pp. 312-326.
Hodis et al., "Estrogen in the Prevention of Atherosclerosis", A Randomized, Double-blind, Placebo-controlled Trial, Ann Intern. Med., vol. 135, 2001, pp. 939-953.
Honer et al., "Glucocortioid Receptor Antagonism by Cyproterone Acetate and RU486", Molecular Pharmacology, vol. 63, No. 5, 2003, pp. 1012-1020.
Hopkins, "Network Pharmacology: The Next Paradigm in Drug Discovery", Nat. Chem. Biol., vol. 4, 2008, pp. 682-690.
Hu et al., "Human Disease-Drug Network Based on Genomic Expression Profiles", PLoS One, vol. 4, Issue 8, e6536, Aug. 2009, 11 pages.
Hu et al., "Methionine Depletion With Recombinant Methioninase: In Vitro and in Vivo Efficacy Against Neuroblastoma and Its Synergism with Chemotherapeutic Drugs", Int. J. Cancer, vol. 124, No. 7, Apr. 2009, pp. 1700-1706.
Huang et al., "Bioinformatics Enrichment Tools: Paths Toward the Comprehensive Functional Analysis of Large Gene Lists", Nucleic Acids Research, vol. 37, No. 1, 2009, pp. 1-13.
Huang et al., "Systematic and Integrative Analysis of Large Gene Lists Using David Bioinformatics Resources", Nature Protoc., vol. 4, 2009, pp. 44-57.
Huang et al., "The NCGC Pharmaceutical Collection: A Comprehensive Resource of Clinically Approved Drugs Enabling Repurposing and Chemical Genomics", Sci. Transl. Med., vol. 3, No. 80, Apr. 27, 2011, 23 pages.
Husson et al., "Retinoic; Acid Normalizes Nuclear Receptor Mediated Hypo-Expression of Proteins Involved in Beta-Amyloid Deposits in the Cerebral Cortex of Vitamin a Deprived Rats", Neurobiol. Dis., vol. 23, 2006, pp. 1-10.
Itil et al., "Thioridazine and Chlordiazepoxide, Alone and Combined, in the Treatment of Chronic Schizophrenia", Compr. Psychiatry, vol. 9, 1968, pp. 633-843.
Ivanovski et al., "The Calcimimetic R-568 Retards Uremiaenhanced Vascular Calcification and Atherosclerosis in Apolipoprotein E Deficient (apoE-/-) Mice", Atherosclerosis, vol. 205, 2009, pp. 55-62.
Iwakura et al., "Molecular Cardiology", Estradiol Enhances Rec. After Myocardial Infa. by Augmenting Incorporation of Bone Marrow-Derived Endothelial Progenitor Cells Into Sites of Ischemia-Induced Neovascularization via Endothelial Nitric Oxide Synthase—Medi. Acti. of Matrix Me, Cir. vol. 113, Mar. 28, 2006, pp. 1605-1614.
Jane el al., "Coadministration of Sorafenib With Rottlerin Potently Inhibits Cell Proliferation and Migration in Human Malignant Glioma Cells", The Journal of Pharmacology Experimental Therapeutics, vol. 319, No. 3, 2006, pp. 1070-1080.
Kahraman et al., "On the Diversity of Physicochemical Environments Experienced by Identical Ligands in Binding Pockets of Unrelated Proteins", Proteins, vol. 78, 2010, pp. 1120-1136.
Kahraman et al., "Shape Variation in Protein Binding Pockets and Their Ligands", J. Mol. Biol., vol. 368, 2007, pp. 283-301.
Kamat et al., "Antitumor Activity of Common Antibiotics Against Superficial Bladder Cancer", Urology, vol. 63, 2004, pp. 457-460.

Kanehisa et al., "Data, Information, Knowledge and Principle: Back to Metabolism in KEGG", Nucleic Acids Research, vol. 42, 2014, pp. D199-D205.
Kanehisa et al., "KEGG: Kyoto Encyclopedia of Genes and Genomes", Nucleic Acids Research, vol. 28, No. 1, 2000, pp. 27-30.
Kast, "Glioblastoma Chemotherapy Adjunct via Potent Serotonin Receptor-7 Inhibition Using Currently Marketed High-affinity Antipsychotic Medicines", British Journal Pharmacology, vol. 161, 2010, pp. 481-487.
Katayama et al., "The Pure Anti-Androgen Bicalutamicle Inhibits Cyclin a Expression Both in Androgen-Dependent and -Independent Cell Lines", International Journal Oncology, vol. 35, 2010, pp. 553-562.
Keiser et al., "Relating Protein Pharmacology by Ligand Chemistry", Nat. Biotechnol., vol. 25, 2007, pp. 197-206.
Kell, "Finding Novel Pharmaceuticals in the Systems Biology Era Using Multiple Effective Drug Targets, Phenotypic Screening and Knowledge of Transporters: Where Drug Discovery Went Wrong and How to Fix It", The FEBS Journal vol. 280, 2013, pp. 5957-5980.
Kellenberger et al, "How to Measure the Similarity Between Protein Ligand-Binding Sites?", Current Computer-Aided Drug Design, vol. 4, No. 3, 2008, pp. 209-220.
Kellenberger et al., "Ranking Targets in Structure-Based Virtual Screening of Three-Dimensional Protein Libraries: Methods and Problems", J. Chem. Inf. Model., vol. 48, 2008, pp. 1014-1025.
Kennedy et al., "Progressive Proximal Spinal and Bulbar Muscular Atrophy of Late Onset: A Sex-linked Recessive Trait", Neurology, vol. 50, 1998, pp. 583-593.
Kessler et al., "Amsacrine Containing Induction Therapy in Elderly Aml Patients: Comparison to Standard Induction Regimens in a Matched-Pair Analysis", Leuk. Res., vol. 32, 2008, pp. 491-494.
Khalilzadeh et al., "Epothilone-Paclitaxel Resistant Leukemic Cells CEM/dEpoB300 are Sensitive to Albendazole: Involvement of Apoptotic Pathways", Biochem. Pharmacol., vol. 74, 2007, pp. 407-441.
Kinnings et al., "Drug Discovery Using Chemical Systems Biology: Repositioning the Safe Medicine Comtan to Treat Multi-Drug and Extensively Drug Resistant Tuberculosis", PLoS Computational Biology, vol. 5, Issue 7, e1000423, Jul. 2009, 10 pages.
Knox et al., "Drugbank 3.0: A Comprehensive Resource for 'Omics' Research on Drugs", Nucleic Acids Research, vol. 39, Nov. 8, 2010, pp. D1035-D1041.
Kondo et al., "Philadelphia Chromosome-Positive Acute Myeloid Leukemia (PH + AML) Treated With Imatinib Mesylate (IM): a Report with Im Plasma Concentration and BCR-ABL Transcript", Leuk. Res., vol. 33, 2009, pp. e137-e138.
Kupsch et al., "Results of a Phase 1 Trial of Sorafenib (Bay 43-9006) in Combination With Oxaliplatin in Patients With Refractory Solid Tumors, Including Colorectal Cancer", Clin. Colorectal Cancer, vol. 5, 2005, pp. 188-196.
Laclette et al., "Inhibition of Tubulin Polymerization by Mebendazole", Biochemical and Biophysical Research Communications, vol. 92, No. 2, Jan. 29, 1980, pp. 417-423.
Lamb et al., "The Connectivity Map: Using Gene-expression Signatures to Connect Small Molecules, Genes, and Disease", Science, vol. 313, 2006, pp. 1929-1935.
Leombruni et al., "Duloxetine in Obese Binge Eater Outpatients: Preliminary Results From a 12-week Open Trial", Hum. Psychopharmacol., vol. 24, 2009, pp. 483-488.
Li et al., "Comparison of Cancer Cell Survival Triggered by Microtubule Damage After Turning Dyrk1B Kinase On and Off", ACS Chem Biol., vol. 9, 2014, pp. 731-742.
Li et al., "TarFisDock: A Web Server for Identifying Drug Targets With Docking Approach", Nucleic Acids Research, vol. 34, 2006, pp. W219-W224.
Liu et al., "BindingDB: A Web-Accessible Database of Experimentally Determined Protein-Ligand Binding Affinities", Nucleic Acids Research, vol. 35, Jan. 2007, pp. D198-D201.
Llacer at al., "Topological Virtual Screening and Pharmacological Test of Novel Cytostatic Drugs", IEJMD, vol. 5, Jun. 2006, pp. 306-319.

(56) References Cited

OTHER PUBLICATIONS

Lounkine et al., "Large-scale Prediction and Testing of Drug Activity on Side-effect Targets", Nature, vol. 486, No. 7403, 2012, pp. 361-367.
Maddika et al., "Akt-Mediated Phosphorylation of CDK2 Regulates Its Dual Role in Cell Cycle Progression and Apoptosis", J. Cell Sci., vol. 121 (Pt 7), 2008, pp. 979-988.
Malinowska et al., "Interlukin-6 Stimulation of Growth of Prostate Cancer in Vitro and in Vivo Through Activation of the Androgen Receptor", Endocrine-Related Cancer, vol. 16, 2009, pp. 155-169.
Marczynski "Gabaergic Deafferentation Hypothesis of Brain Aging and Alzheimer's Disease; Pharmacologic Profile of the Benzodiazepine Antagonist, Flumazenil", Rev. Neuroscience, vol. 6, 1995, pp. 221-258.
Martarelli et al., "Mebendazole Inhibits Growth of Human Adrenocortical Carcinoma Cell Lines Implanted in Nude Mice", Cancer Chemother Pharmacol., vol. 61, 2008, pp. 809-817.
Martinelli et al., "Synergistic Antitumor Activity of Sorafenib in Combination With Epidermal Growth Factor Receptor Inhibitors in Colorectal and Lung Cancer Cells", Clinical Cancer Research, vol. 16, No. 20. Oct. 15, 2010, pp. 4990-5001.
Medina-Franco et al., "Shifting from the Single to Multitarget Paradigm in Drug Discovery", Drug Discovery Today, vol. 18, May 2013, pp. 495-501.
Meslamani et al., "Computational Profiling of Bioactive Compounds Using a Target-Dependent Composite Workflow", J. Chem. Inf. Model, vol. 53, 2013, pp. 2322-2333.
Meslamani et al., "sc-PDB: A Database for Identifying Variations and Multiplicity of 'Druggable' Binding Sites in Proteins", Bioinformatics, vol. 27, No. 9, 2011, pp. 1324-1326.
Mogensen et al., "Randomised Controlled Trial of Dual Blockade of Renin-Angiotensin System in Patients With Hypertension, Microalbuminuria, and Non-Insulin Dependent Diabetes: The Candesartan and Lisinopril Microalbuminuria (Calm) Study", BMJ, vol. 321, Dec. 9, 2000, pp. 1440-1444.
Morgillo et al., "Antitumor Activity of Sorafenib in Human Cancer Cell Lines With Acquired Resistance to EGFR and VEGFR Tyrosine Kinase Inhibitors", PLoS One, vol. 6, Issue 12, e28841, 2011, 9 pages.
Muegge "Synergies of Virtual Screening Approaches", Mini. Rev. Med. Chem., vol. 8, 2008, pp. 927-933.
Mukhopadhyay et al., "Mebendazole Elicits a Potent Antitumor Effect on Human Cancer Cell Lines Both in Vitro and in Vivo", Clinical Cancer Research, vol. 8, No. 9, Sep. 2002, pp. 2963-2969.
Nellemann et al., "The Combined Effects of Vinclozolin and Procymidone Do Not Deviate From Expected Additivity in Vitro and in Vivo", Toxicological Science, vol. 71, 2003, pp. 251-262.
Nygren et al., "Repositioning of the Antihelminthic Drug Mebendazole for the Treatment of Colon Cancer", J Cancer Res Clin Oncol, vol. 139, 2013, pp. 2133-2140.
Oger et al., "Differential Effects of Oral and Transdermal Estrogen/Progesterone Regimens on Sensitivity to Activated Protein C Among Postmenopausal Women", A Randomized Trial, Arterioscler Thromb Vasc Biol. vol. 23, 2003, pp. 1671-1076.
Ohnishi, "PML-RARalpha Inhibitors (ATRA, tamibaroten, arsenic troxide) for Acute Promyelocytic Leukemia", Int. J. Clin. Oncol., vol. 12, 2007, pp. 313-317.
Olsson , "Stroke Prevention With the Oral Direct Thrombin Inhibitor Ximelagatran Compared With Warfarin in Patients With Non-valvular Atrial Fibrillation (Sportif III): Randomised Controlled Trial", Lancet, vol. 362, 2003, pp. 1691-1698.
Ozawa et al., "Oral High-dose Phenobarbital Therapy for Early Infantile Epileptic Encephalopathy", Pediatr. Neurol., vol. 26, 2002, pp. 222-224.
Paul et al., "Recovering the True Targets of Specific Ligands by Virtual Screening of the Protein Data Bank", Proteins, vol. 54, 2004, pp. 671-680.
International Application No. PCT/US2016/035639, "International Preliminary Report on Patentability", dated Dec. 21, 2017, 8 pages.
International Application No. PCT/US2016/035639, "International Search Report and Written Opinion", dated Sep. 13, 2016, 11 pages.
Pereira et al., "Maximizing the Therapeutic Window of an Antimicrobial Drug by Imparting Mitochondrial Sequestration in Human Cells", J. Am. Chem. Soc., vol. 133, 2011, pp. 3260-3263.
Pourgholami et al., "Albendazole Inhibits Endothelial Cell Migration, Tube Formation, Vasopermeability, VEGF Receptor-2 Expression and Suppresses Retinal Neovascularization in ROP Model of Angiogenesis", Biochem. Biophys. Res. Commun., vol. 397, 2010, pp. 729-734.
Pourgholami et al., "Antitumor Activity of Albendazole Against the Human Colorectal Cancer Cell Line HT-29: In Vitro and in a Xenograft Model of Peritoneal Carcinomatosis", Cancer Chemother Pharmacol., vol. 55, 2005, pp. 425-432.
Pourgholami et al., "In Vitro and In Vivo Suppression of Growth of Hepatocellular Carcinoma Cells by Albendazole", Cancer Lett., vol. 165, 2001, pp. 43-49.
Pourgholami et al., "Inhibition of Cell Proliferation, Vascular Endothelial Growth Factor and Tumor Growth by Albendazole,", Cancer Invest, vol. 27, 2009, pp. 171-177.
Pourgholami et al., "Potent Inhibition of Tumoral Hypoxia-Inducible Factor 1alpha by Albendazole", BMC Cancer, vol. 10, No. 143, 2010, 7 pages.
Pujol et al., "Unveiling the Role of Network and Systems Biology in Drug Discovery", Trends Pharmacol. Sci., vol. 31, 2010, pp. 115-123.
Rajkumar et al., "Advances in the Treatment of Amyloidosis", N. Engl. J. Med., vol. 356, 2007, pp. 2413-2415.
Richards et al., "Comparison of the Airway Response to Eye Drops of Timolol and Its Isomer L-714,465 in Asthmatic Subjects", Br. J. Clin. Pharmac. vol. 24, 1987, pp. 485-491.
Sasaki et al., "The Anthelmintic Drug Mebendazole Induces Mitotic Arrest and Apoptosis by Depolymerizing Tubulin in Non-Small Cell Lung Cancer Cells", Molecular Cancer Therapeutics, vol. 1, No. 13, Nov. 2002, pp. 1201-1209.
Sasvari-Szekely et al., "Activation of Deoxycytidine Kinase During Inhibition of DNA Synthesis by 2-Chloro-2'-Deoxyadenosine (Cladribine) in Human lymphocytes", Biochem. Pharmacol., vol. 56, 1998, pp. 1175-1179.
Schadt et al., "A Network View of Disease and Compound Screening", Nat Rev Drug Discovery, vol. 8, 2009, pp. 286-295.
Serrels et al., "Identification of Potential Biomarkers for Measuring Inhibition of Src Kinase Activity in Colon Cancer Cells Following Treatment With Dasatinib", Mol. Cancer Ther., vol. 5, No. 12, Dec. 2006, pp. 3014-3022.
Seyfried et al., "Cancer as a Metabolic Disease", Nutrition Metabolism, vol. 7, No. 7, 2010, 22 pages.
Shimizu et al., "Papaverine Combined with Prostaglandin E2 Synergistically Induces Neuron-like Morphological Changes and Decrease of Malignancy in Human Prostatic Cancer LNCaP Cells", Anticancer Res., vol. 20, 2000, pp. 761-767.
Silberstein et al., "Migraine, Menopause and Hormonal Replacement Therapy", Cephalagia, vol. 20, 2000, pp. 214-221.
Smith et al., "Cognitive and Antismoking Effects of Varenicline in Patients With Schizophrenia or Schizoaffective Disorder", Shizophr Res., vol. 110, 2009, pp. 149-155.
Swinney et al., "How Were New Medicines Discovered?", Nature Reviews, Drug Discovery, vol. 10, 2011, pp. 507-519.
Syrbe et al., "Effects of the Angiotensin II Type 1 Receptor Antagonist Telmisartan on Monocyte Adhesion and Actvation in Patients With Essential Hypertension", Hypertens Res, vol. 30, No. 6, 2007, pp. 521-528.
Takezawa et al., "Sorafenib Inhibits Non-Small Cell Lung Cancer Cell Growth by Targeting B-RAF in Kras Wild-Type Cells and C-RAF in KRAS Mutant Cells", Cancer Research, vol. 69, No. 16, Aug. 15, 2009, pp. 6515-6521.
Tan et al., "Metabonomics Identifies Serum Metabolite Markers of Colorectal Cancer", J. Proteome Res., vol. 12, No. 6, Jun. 2013, pp. 3000-3009.
Tang et al., "Crystal Structure of Pyridoxal Kinase in Complex With Roscovitine and Derivatives", The Journal of Biological Chemistry, vol. 280, No. 35, Sep. 2005, pp. 31220-31229.

(56) References Cited

OTHER PUBLICATIONS

Tannock et al., "Docetaxel Plus Prednisone of Mitoxantrone Plus Prednisone for Advanced Prostate Cancer", The New England Journal of Medicine, vol. 351, No. 15, Oct. 7, 2004 pp. 1502-1512.

Thacher et al., "Nutritional Rickets in Ichthyosis and Response to Calcipotriene", Pediatrics, vol. 114, No. 1, Jul. 1, 2004, pp. e119-e123.

Tonini, "Recurrent Scrotal Hemangiomas During Treatment with Sunitinib", Journal of Clinical Oncology, vol. 28, Np. 35, Dec. 10, 2010, pp. e737-e738.

Trost et al., "No Human Protein Is Exempt from Bacterial Motifs, Not Even One", Self Nonself, vol. 1, Issue 4, 2010, pp. 328-334.

Tsang et al..; "Arginase Deficiency With New Phenotype and a Novel Mutation: Contemporary Summary", Pediatr. Neurol., vol. 47, 2012, pp. 263-269.

Warner et al., "Identification of FDA-Approved Drugs That Computationally Bind to MDM2", Chem. Biol. Drug Des., vol. 80. No. 4, Oct. 2012, pp. 631-637.

Weimann et al., "Studies on Wound Healing: Effects of Calcium D-Pantothenate on the Migration, Proliferation and Protein Synthesis of Human Dermal Fibroblasts in Culture", Int. J. Vitam. Nutr. Research, vol. 69, 1999, pp. 113-119.

White et al., "Antihypertensive Effects of Drospirenone With 17beta-Estradiol, A Novel Hormone Treatment in Postmenopausal Women With Stage 1 Hypertension", Circulation, vol. 112, 2005, pp. 1979-1984.

Wishart et al., "HMDB 3.0—The Human Metabolome Database in 2013", Nucleic Acids Research, vol. 41, 2013, pp. D801-D807.

Yamashita et al., "Giant Cavernous Hepatic Hemangioma Shrunk by Use of Sorafenib", Clin. J. Gastroenterol, vol. 6, 2013, pp. 55-62.

Yang et al., "Harvesting Candidate Genes Responsible for Serious Adverse Drug Reactions From a Chemical-protein Interactome", PLoS Computational Biology, vol. 5, issue 7, e1000441, Jul. 2009, 12 pages.

Yildirim et al., "Drug-Target Network", Nat. Biotechnol., vol. 25, 2007, pp. 1119-1126.

Zahler et al., "Inverse in Silico Screening for Identification of Kinase Inhibitor Targets", Chemistry and Biology, vol. 14, Nov. 2007, pp. 1207-1214.

Zajac et al., "Kennedy's Disease: Clinical Significance of Tandem Repeats in the Androgen Receptor", Adv. Exp. Med. Biol., vol. 769, 2012, pp. 153-168.

Zhang et al., "Indomethacin Induces Apoptosis and Inhibits Proliferation in Chronic Myeloid Leukemia Cells", Leuk. Res., vol. 24, 2000, pp. 385-392.

Zuanetti et al., "Effect of the Ace Inhibitor Lisinopril on Mortality in Diabetic Patients With Acute Myocardial Infarction", Data From the GISSI-3 Study Circulation, vol. 96, Dec. 16, 1997, pp. 4239-4245.

\* cited by examiner

PREDICTING DRUG-TARGET INTERACTIONS AND USES FOR DRUG REPOSITIONING AND REPURPOSING

CROSS REFERENCE TO RELATED APPLICATION

This application claims the benefit of priority to U.S. Application No. 62/172,639, entitled "PREDICTING DRUG-TARGET INTERACTIONS AND USES FOR DRUG REPOSITIONING AND REPURPOSING," filed Jun. 8, 2015, the entire contents of which are incorporated herein by reference for all purposes.

STATEMENT AS TO RIGHTS TO INVENTIONS MADE UNDER FEDERALLY SPONSORED RESEARCH AND DEVELOPMENT

This invention was made with U.S. government support under grant numbers BC062416, BC096277 (SB, SD), R01 CA 170653 (SB, SD), awarded by the Department of Defense; and under grant number NIH-P30 CA51008, awarded by the National Institutes of Health. The government has certain rights in the invention.

BACKGROUND

Traditional methods of drug discovery face formidable scientific and regulatory obstacles resulting in the passage of many years and many failures from the discovery of a target to the clinical application of a novel patentable drug designed to inhibit or activate its function. There has been a marked decline in the willingness of the pharmaceutical industry to invest in drug discovery programs. With the emergence of systems biology approaches many more new drug targets have been identified and validated. However, drug development for these new targets can be time consuming and prohibitively expensive, leading to the concept of drug repositioning in which existing approved compounds are repurposed for another target/disease. There are clear advantages to this approach, including a dramatic reduction in time, expense, and safety concerns.

A number of existing approved drugs can serve as effective therapies for diseases other than those for which they were approved. Recently, the National Institutes of Health (NIH) has emphasized the importance of drug repositioning and deposited more than 27,000 active pharmaceutical ingredients in the Chemical Genomics Center (NCGC) database to encourage public screening. To date, screening is usually achieved by high throughput chemical screening or transcriptome matching. Other methods include phenotypic screening, protein-protein interaction assays, drug annotation technologies, high-throughput screening using cell-based disease models, gene activity mapping, ligand-based cheminformatics approaches, and in vivo animal models of diseases. However, experimentally testing all approved drugs against all targets is extremely expensive, as well as technically unrealizable.

An additional challenge of these screening studies is that after one gets a "hit," the rational mechanism of action must still be deduced and tested. To address this, computational approaches based on drug regulated gene expression, side effect profile, and protein or chemical similarity, have been developed. Using high performance computing, high-throughput computational drug-target docking and screening are now also feasible. However, current methods are only able to predict a rough estimation of the free energy of binding and further suffer from high false positive rates and low rates of drug-target association prediction.

It is therefore desirable to provide new computational systems and methods to more accurately identify drugs that have a high interaction with targets.

BRIEF SUMMARY

Described herein are methods of predicting drug-target interactions and methods of using the information for drug repurposing. Embodiments described herein can combine different descriptors including, for example, atom pair, shape, topology and chemical signatures, physico-chemical functional descriptors, contact points of the ligand and the target protein, chemical similarity, and docking score to identify a ligand that interacts with a target. Atom pair (AP) similarity scores may be calculated using an AP similarity Tanimoto coefficient. Additionally, descriptors used may be normalized using a rigorous method. The inclusion of atom pair scores and the rigorous normalization method improve the accuracy of methods compared to methods without atom pair scores and rigorous normalization.

Other embodiments are directed to systems and computer-readable media associated with methods described herein. The details of one or more embodiments are set forth in the description below. Other features, objects, and advantages will be apparent from the description and from the claims.

A better understanding of the nature and advantages of embodiments of the present technology may be gained with reference to the following detailed description and the accompanying drawings.

DETAILED DESCRIPTION

Figure 1:
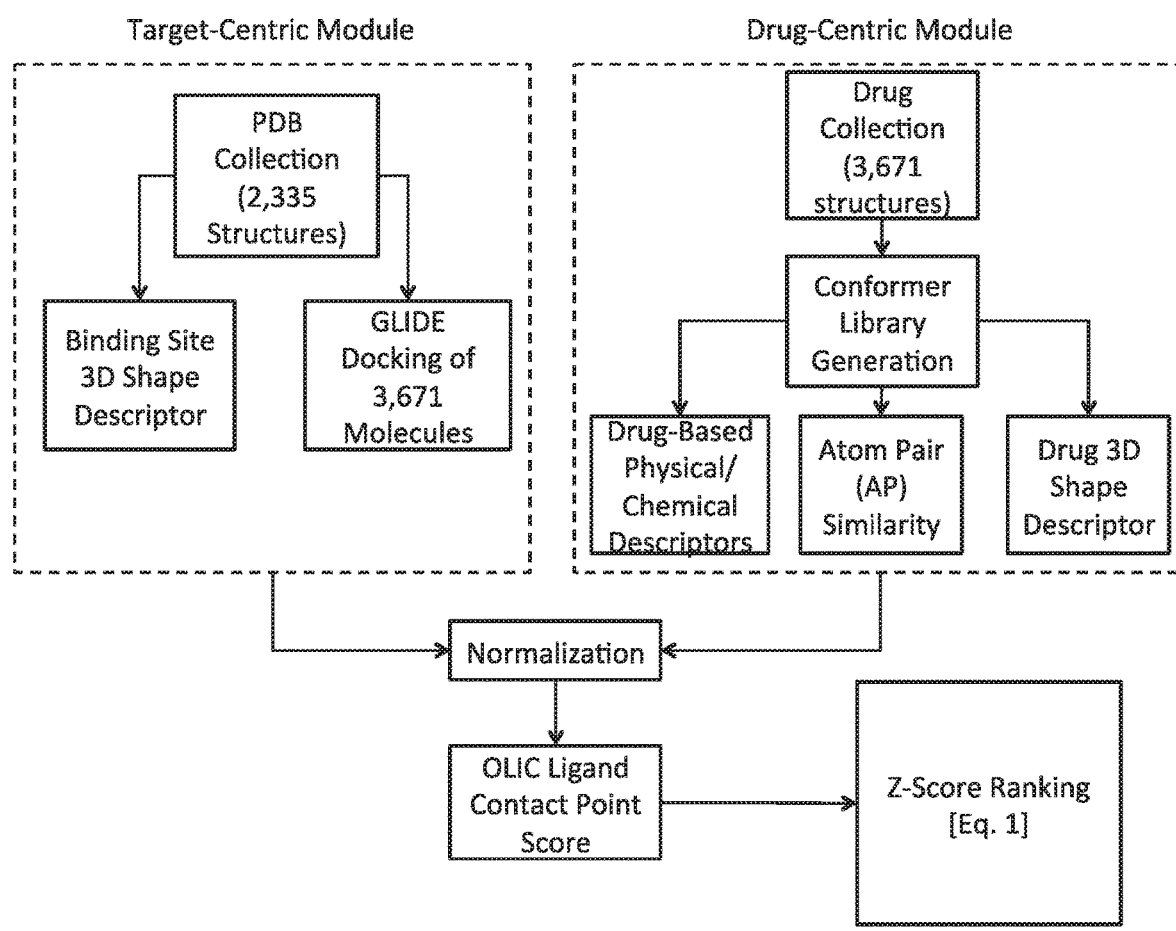
FIG. 1 shows a workflow algorithm for the methods of identifying protein-drug interactions according to embodiments of the present technology.

Described herein are methods for predicting drug-target interactions, such as, for example, the molecule of best fit for a target. Embodiments can provide a comprehensive prediction method, which may collectively be called "RepurposeVS," that can reduce false positive predictions and enrich for the highest confidence drug-target interactions. Conventional techniques screened FDA drugs using either chemical similarity or docking with stringent scoring criteria. In contrast, embodiments described herein can combine different descriptors including, for example, atom pair similarity, shape, topology and chemical signatures, physico-chemical functional descriptors, contact points of the ligand and the target protein, chemical similarity, and docking score. Descriptors can be trained with template knowledge; match and fit of the signatures identified; and the data stream lined.

Some embodiments can be receptor-centric (i.e., focuses on the target receptor). Other embodiments can be ligand-centric (i.e., focuses on ligands). Potential drug-target interactions are predicted with accuracy. For example, embodiments can predict drug-target associations with greater than 80% accuracy (e.g., greater than 85% accuracy, greater than 89% accuracy, greater than 90% accuracy, or greater than 91% accuracy) for the majority of drugs.

Drug repurposing—the process of utilizing drugs approved for one indication for another—is an efficient method for bolstering the pharmaceutical pipeline. Given that approved drugs have known well-tolerated toxicity profiles, they can, therefore, be streamlined back into the development pipeline directly at phase II. Despite some successes, drug repurposing remains a challenge for two main reasons: (1) validating druggable therapeutic target(s) associated with the disease, and (2) confidently establishing the repertoire of protein target interactions for the FDA approved drug set. Embodiments described herein may address the latter aspect.

A variety of methods for establishing drug-target interactions are employed in both academia and industry. High-throughput screening (HTS) strategies are used for establishing interactions for large drug libraries against protein targets of interest. These approaches, however, have multiple obstacles. These include the financial cost per assay run, development of appropriate screening assays, maintaining biochemical relevance of the target given the assay (i.e. target immobilization in 96-well plates may alter binding site properties), among others. The amount of potential druggable disease-related targets is also exponentially increasing along with the number of synthesizable drugs. Creating the vast possible drug-target space of true interactions and further narrowing it to that of physiologic- and disease-relevance remains a great challenge.

Computer-aided methods may allow for a substantial increase in efficiency in establishing drug-target interactions and are constantly becoming more accurate as the biophysical mechanisms behind molecular recognition become better understood. Such methods are typically used in virtual screenings against a protein target of interest, where large drug libraries (>1,000,000 structures) are subjected to an algorithm that quantifies the drugs' "fit" into the binding site. The first few hundred or thousand drugs are then validated experimentally, and the potential drug-target space has been drastically reduced to that with the greatest biological plausibility.

Many efforts for computationally predicting drug-target interactions exist, spanning both chemo-centric and target-based methodologies. Chemo-centric approaches utilize physical and chemical information obtained from ligands. Some approaches relate receptors based on the chemical similarity as well as shape similarity between ligands. Large public databases that aid in extracting ligand-based data for informatics also exist. Target-based approaches, on the other hand, rely on docking or binding site similarity. Docking has driven some successful drug repurposing attempts, but scoring functions are generally considered inaccurate in calculating free energies of binding due to difficulty in predicting bioactive poses and variable contributions of weak interactions. Alternatively, binding site comparison methods are implemented under the premise that similar binding sites should bind similar molecules. The use of binding site similarities has been successful in identifying novel targets for known drugs under the assumption that drugs interact with proteins containing similar binding sites.

While chemo-centric and target-based methods have their own strengths and limitations, few computational methods attempt to combine ligand- and protein-based approaches. In this work, methods, including RepurposeVS, may describe a comprehensive method for predicting FDA approved and experimental drug-protein target interactions through computationally efficient virtual screenings. RepurposeVS may combine high-throughput docking with quantified shape, atom pair, and other descriptor similarity information of query drugs to reference experimentally derived crystal structure complexes. Furthermore, the utilized normalization procedure may provide biological context of binding and allows for cross-protein comparison of drug binding signatures instead of protein-specific rank-ordering of drugs. This may enable a standardized prioritization of predicted drug-target signatures for the entire proteome cohort in a study and the future incorporation of new signatures when novel protein target structures become available.

Optionally, methods may include computationally obtaining and processing three-dimensional protein structures, computationally docking a drug into the protein structure, comparing atom pair similarities for reference ligands and test ligands, generating and quantifying receptor and ligand descriptors, quantifying the receptor and ligand descriptors, and calculating a comprehensive score according to the following equation:

$$Z(q, p, r) = \omega_j Y(p, q) + \omega_k P(r, q) + \sum_{m=1}^{M} [\omega_m f_m(p, q) + \omega'_m f'_m(r, qp, q)] + \sum_{n=1}^{N} X_n(r, q) + CS(OLIC),$$

where the comprehensive score can indicate the degree of protein-drug interaction. In some examples, the comprehensive score can be used to determine the fit of the drug. Various embodiments can exclude one or more terms from the above equation when calculating the score.

Optionally, embodiments for predicting the new use for the known drug can be enhanced by using information obtained by querying a database with data obtained from other methods for identifying drug targets. Novel analogues of the known drug can be developed to treat diseases and disorders associated with the identified drug target.

To assess accuracy, RepurposeVS was compared to the GLIDE docking algorithm in virtual screening experiments for prioritization of known drug binders for multiple pharmaceutically relevant protein targets. As RepurposeVS is a drug repurposing-driven method, the drug set chosen for benchmarking includes 3,671 FDA approved and experimental drugs. This drug set is composed of diverse chemical structures and chemotypes, as well as streamlines the generation of drug repurposing hypotheses for later experimental testing. Although benchmarks for virtual screening methods typically utilize the Database of Decoys (DUD-E), we are focused on drug repurposing and therefore the ability of RepurposeVS to enrich for actives from an approved drug set rather than a chemical set of closely related analogues that may or may not be clinically relevant. RepurposeVS provided the greatest enrichment for known active drugs and was then scaled up to predict drug-target signatures across 2,335 human protein targets. Cursory global validation across the entire protein target set was then achieved by recapitulating the phenomenon of similarly shaped protein pockets binding drugs of similar shape. Biological validation was further obtained for the anti-hookworm drug mebendazole via kinase binding assays, thus providing further evidence to its anti-cancer efficacy for repurposing. Finally, RepurposeVS was used to explore the entire potential drug repurposing space by devising a "repurposing potential score". With its high accuracy and ease of implementation, RepurposeVS is an efficient computational method for the accurate prediction of drug-protein target signatures to drive drug repurposing efforts forward.

I. Predicting Drug-Target Interactions

A. Drug and Protein Target Dataset

Drugs were obtained from the DrugBank, FDA and BindingDB. LigPrep was used to prepare and minimize drug structures at neutral pH of 7.0. Human protein target crystal structures containing a reference drug in the binding pocket with X-ray resolution <2.5 angstrom were chosen from RCSB (www.rcsb.org). After processing, the dataset included 3,671 drugs and 2,335 protein target crystal structures. Known active drugs for the benchmark protein targets HSP90A (PDB: 4O05), CA4 (PDB: 3FW3), ALDR1 (PDB: 3RX3), ACE (PDB: 1O86), PPARG (PDB: 3VSO), ADRB2 (PDB: 3NYA), VEGFR2 (PDB: 2P2H), ESR1 (PDB: 3ERD), AR (PDB: 3L3Z), BACE1 (PDB: 3VF3), GR (PDB: 4P6X), and HMGCR (PDB: 1HWK) were obtained via DrugBank annotations.

B. RepurposeVS Equation

The workflow for RepurposeVS may be outlined in FIG. 1. A 3D comprehensive conformer library was generated using ConfGen for each drug. From this library, the conformer whose 3D shape was most similar to that of the reference ligand bioactive pose was chosen for all subsequent steps. GLIDE docking was performed to obtain free energies of binding, QikProp was used for generating ligand-based 2D descriptors, and 3D shape descriptors for drug and protein binding sites were generated using spherical harmonics expansion coefficients Java software package provided to us by the Thornton group. Reference-occupied protein target pocket shapes were determined using protomol information from sc-PDB. Atom Pair (AP) similarity normalized scores were calculated directly using Strike.

The RepurposeVS Z-score ranking equation for a query drug q against protein target p with reference drug r may be as follows:

$$Z(q, p, r) = \omega_j Y(p, q) + \omega_k P(r, q) + \sum_{m=1}^{1}[\omega_m f_m(p, q) + \omega'_m f'_m(r, q)] + \sum_{n=1}^{N} X_n(r, q) + CS(OLIC) \quad (1)$$

In equation (1), Y represents the rigorously normalized docking score based on the method outlined in Section 2.2.1 below with weight $\omega_j$=4. P represents the normalized AP similarity Tanimoto coefficient ($T_c$) of a query drug q to the reference drug r along with its designated weight ($\omega_k$=4).

The first summation corresponds to the shape similarity metric composed of two functions: (1) $\omega_m f_m(p,q)\omega_m f_m(\sigma_p, \sigma_l)$, where $f_m$ is the shape function corresponding to a similarity quantification between pocket shape of the protein target p and the query drug q with weighting factor $\omega_m$=2, and (2) $\omega'_m f'_m(r,q)$, where $f'_m$ is a shape function corresponding to a similarity quantification between reference drug shape r and query drug shape q with weighting factor $\omega'_m$=2. Shape similarities are represented as Euclidean distances between the spherical harmonics expansion coefficients, as described in. The second summation term corresponds to the combined similarity of N=10 query drug-based descriptors terms ($X_n$) to reference drug r. Normalized $T_c$ scores were calculated for the following descriptors: (1) number of H-bond acceptors, (2) number of H-bond donors, (3) dipole, (4) electron affinity, (5) globularity, (6) molecular weight, (7) ClogP, (8) number of rotatable bonds, (9) solvent-accessible surface area, and (10) volume. ClogP is a measure of the lipophilicity and is a partition coefficient of a molecule between an aqueous phase and a lipohphilic phase.

The CS(OLIC) term is a correction term called "optimal ligand interaction correction" (OLIC), an algorithm that obtains a better estimate of drug-protein interactions on the reference binding site by assuming that drugs will have similar experimental activity if their interaction involves similar binding site residues and makes similar interaction patterns to the reference drug. Equation (2) may be used to determine binding site energies for reference drug, and equation (3) may be used to determine binding site energies for the query drugs (3):

$$S(OLIC - r)_p = \sum_{n=1}^{NR} \omega_n E_{n,p} \quad (2)$$

$$S(OLIC - q)_{q,p} = \sum_{n=1}^{NQ} \omega_n E_{n,q,p} \quad (3)$$

The sums are over the number of contact points NR or NQ between protein p and its reference drug or query drugs, respectively. Contact points for drugs are described as those that overlap with established reference drug-protein contacts. Drugs that match or cover most of the interactions as that of the reference scored higher. Their corresponding energies are evaluated and compared with the energy of the reference drug. Energy of the test ligands scored higher if it is close or higher than the energy of the reference drug. The $E_{n,p}$ corresponds to energy for the nth contact point for the reference drug-protein complex (p,r). The $E_{n,q,p}$ term corresponds to energy for the nth contact point for the qth query drug and protein p. Weighting factors specific to each contact point used and are dependent on the particular drug-target complex.

The correction term CS(OLIC) has been determined as a difference between the two sums in equation (4):

$$CS(OLIC)=S(OLIC-r)_p-S(OLIC-q)_{q,p} \quad (4)$$

The additive combination of the aforementioned normalized terms with their respective weights results in the final RepurposeVS comprehensive Z-score (Equation (1)) to rank drugs for a given target.

C. Methods

Figure 2:
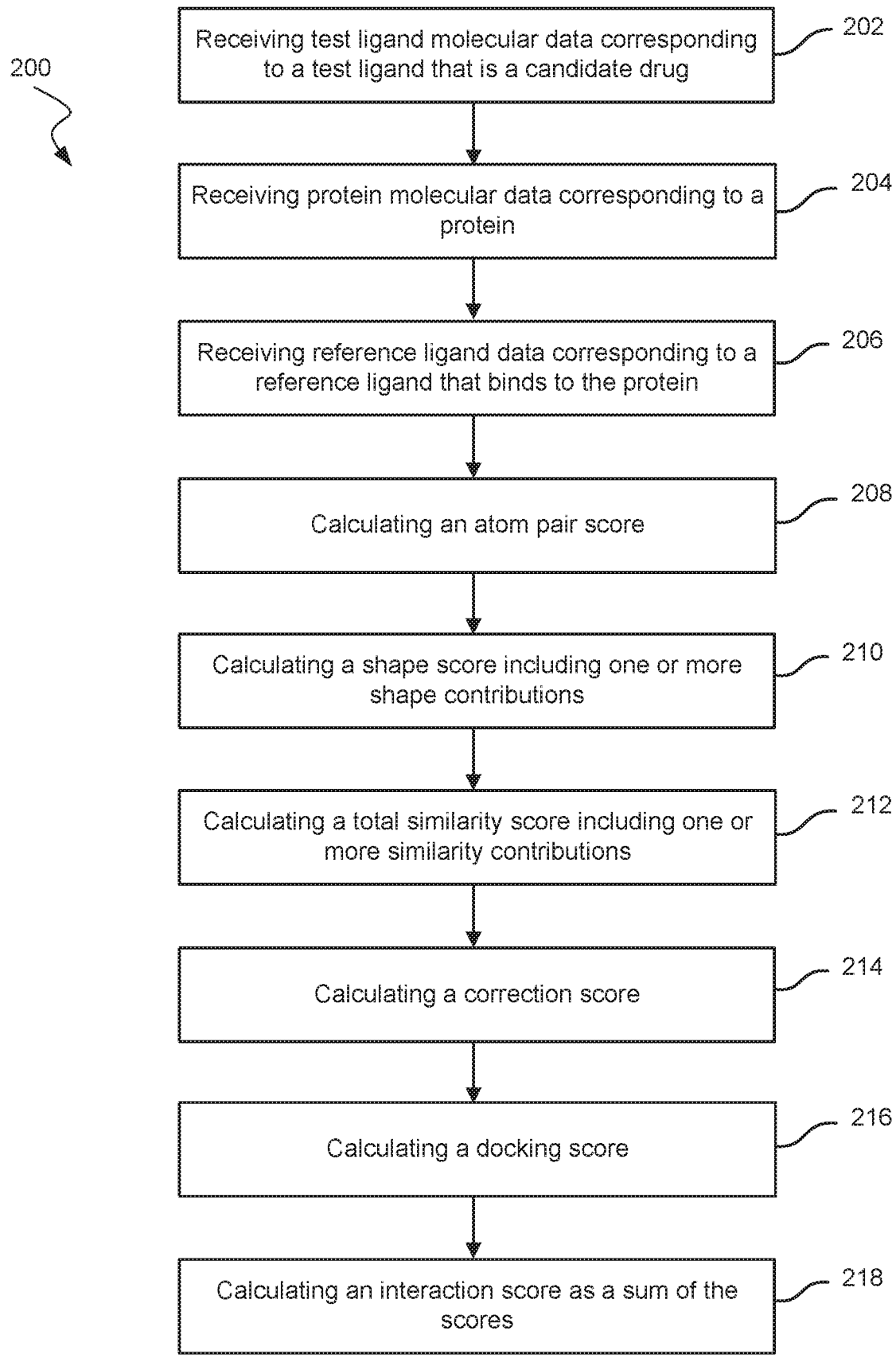
FIG. 2 is a flowchart of a method 200 for identifying protein-drug interactions according to embodiments of the present technology.

FIG. 2 is a flowchart of a method 200 for identifying protein-drug interactions according to embodiments of the present technology. Method 200 may be performed with a computer system. Various scores calculated in method 200 may be optional.

At block 202, test ligand molecular data corresponding to a test ligand that is a candidate drug is received. The test ligand molecular data can include physical information about bonds and atoms of the test ligand, chemical information such as solvent information, electrostatic information such as a dipole.

At block 204, protein molecular data corresponding to a protein is receiving. The protein molecular data can include three-dimensional protein structures of the protein. As other examples, physical and electrostatic information can also be received.

At block 206, reference ligand data corresponding to a reference ligand that binds to the protein is received. In one embodiment, at least some of the reference ligand data is obtained from a complex of the reference ligand bound to the protein. For example, x-ray information of a complex of the reference ligand bound to the protein can be received.

At block 208, an atom pair score of the reference ligand and the test ligand is calculated. For example, the second term in Equation (1) can be calculated. The atom pair score may be calculated based on different atom descriptors described herein.

At block 210, a shape score including one or more shape contributions is calculated. For example, the first summation term in Equation (1) can be calculated. Each shape contribution corresponds to a respective shape descriptor (e.g., shape, volume, tortuosity, other geometrical characteristics, etc.). A respective contribution (e.g., mth contribution) includes a first part and a second part. The first part provides a first shape score from a first respective shape function (e.g., $f_m(p,q)$) of the protein and the test ligand corresponding to the respective shape descriptor. The second part provides a second shape score from a second respective shape function (e.g., $f_m'(r,q)$) of the reference ligand and the test ligand corresponding to the respective shape descriptor. The shape score can be determined as a sum of the respective first and second shape scores of the contribution(s).

At block 212, a total similarity score including one or more similarity contributions is calculated. Each similarity contribution corresponds to a respective similarity descriptor (e.g., number of rotatable bonds or SASA). A respective similarity contribution provides a respective similarity score (e.g., determined by $X_n(r,q)$) between a respective similarity function of the test ligand (e.g., function providing SASA of test ligand) and the respective similarity function of the reference ligand (function providing SASA of reference ligand).

A principal component analysis can determine the most important descriptors for the shape and similarity descriptors. In some embodiments, only these most important descriptors are used. In one embodiment, descriptors for shape, volume, rotor (number of rotatable bonds), acceptHB (number of hydrogen-bond acceptors), have the most impact on the resulting interaction score.

At block 214, a correction score is calculated. The correction score can be a difference between a first sum and a second sum, where the first sum is of energies of contact points between the reference ligand and the protein and the second sum is of energies of contact points between the test ligand and the protein. The different contact points can have different energies, and be weighted differently.

At block 216, a docking score can be calculated. The docking score can be computed using techniques known to one skilled in the art. The docking score can be negative. A normalization factor can provide a docking score that is positive and between 0 and 1.

At block 218, an interaction score is calculated. The interaction score can include a sum of the shape score, the total similarity score, and the correction score, as well as the docking score. The interaction score can be compared to a threshold value to determine whether or not an interaction exists. For example, if the interaction score is above the threshold value, an interaction can be identified as existing, since the level of binding is predicted to be high. The threshold value may be a score value (e.g., 0.7 or other numerical value). In another embodiment, a plurality of interaction scores for a plurality of test ligand and protein combinations can be determined, and a ranking of the plurality of interaction scores can be performed. Then, the ranking can be used as a threshold value. Interaction scores above a certain rank can identify an interaction as existing. The rank can be determined as an absolute value, such as 10 or 40. The rank can also be determined as a percentage, e.g., in the top 10%.

D. Rigorous Normalization Procedure of Terms

RepurposeVS may contain distinct parameters in Equation (1) that may be represented in different units, which correspondingly contain very different raw numeric ranges. For example, docking scores may be expressed in kJ/mol where small changes in number correspond to large changes in the free energies of binding. Shape similarity terms may be quantified by Euclidean distances and, therefore, function on an independent range of values that may be incompatible with other terms in the equation. Consequently, to better allow RepurposeVS parameters to be compared and weighted intelligently, raw values for the docking score and shape similarity terms Y, $f_m$, and $f'_m$ may be normalized onto the $N(x):R \to (0,1)$ unit range using a sigmoid function to preserve order and provide symmetry. The normalization function may be defined in Equation (5):

$$N_\alpha(x) = 1 - |1 - S_\alpha(x)| \tag{5}$$

where x is the raw parameter, S(x) is a sigmoid function, and α is a tunable scalar coefficient chosen to maximize the information-preserving variance in the image of N(x) in Equation (5). Since the range varied significantly between parameters, the coefficient α varied as well.

For the sigmoid function, the hyperbolic tangent function is chosen because it may be well-behaved and computationally tractable, yielding Equation (6). Some RepurposeVS parameters may require subtly different normalization properties. Hence, Equation (6) may be re-expressed for easier modification in special normalization cases. Expressing Equation (6) in terms of the simpler logistic function L, shown in Equation (7), yields the equivalent function in Equation (8):

$$N_\alpha(x) = 1 - \left|\tanh\left(\frac{\alpha x}{2}\right)\right| \tag{6}$$

$$L_\alpha(x) = \frac{1}{1+e^{-\alpha x}} \tag{7}$$

$$N_\alpha(x) = 1 + 2 * \left|\frac{1}{2} - L_\alpha(x)\right| \tag{8}$$

To check the information preserving quality of this normalization, histograms of both the un-normalized, or raw (FIG. 3A), and normalized population distributions (FIG. 3B) were formed for the shape similarity parameter using α=0.1.

Figure 3A:
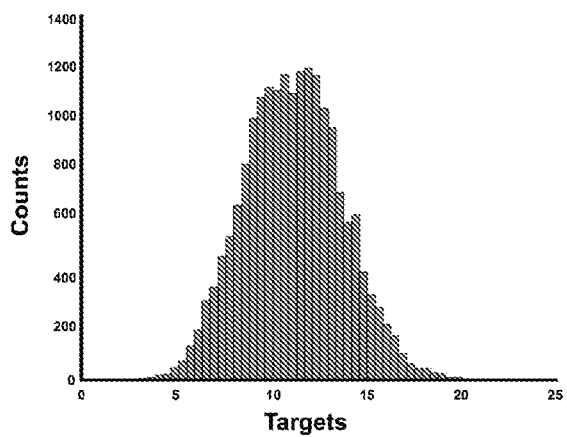
FIGS. 3A, 3B, and 3C show graphs of the effect of normalization of parameters according to embodiments of the present technology.
Figure 3B:
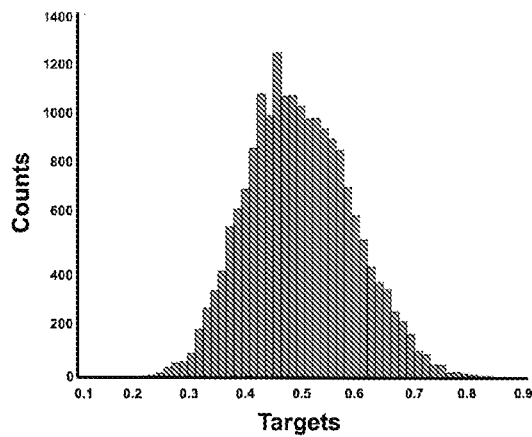

FIG. 3A shows a histogram of raw (non-normalized) scores for post-docking shape similarity Euclidean distance calculations of 2,207 unique drug-protein target pairs. The Y-axis shows counts of data points versus X-axis Euclidean distances using a bin-width of 0.5. FIG. 3B shows a histogram of normalized scores for the same 2,207 shape similarity calculations shown in FIG. 3A. The normalization equation is shown in Equation (14). The normalization may preserve the Gaussian shape of the distribution, and centers the new distribution on the 0.5 mid-point of the 0-1 unit range.

FIG. 3A shows that in this case normalization results in a good fit for a symmetric and centered (at 0.5) Gaussian distribution implying that the normalized data will be statistically well behaved. Based on a comparison of the un-normalized to normalized distributions, the input distribution was not significantly distorted by the normalization function N(x).

Figure 3C:
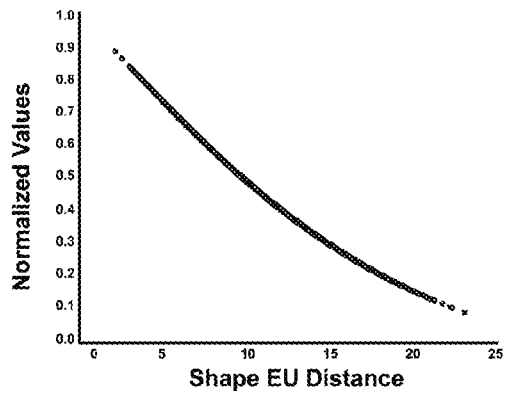

A scatterplot of the un-normalized shape parameter versus the normalized shape parameter was also formed (FIG. 3C). The scatterplot shows the relationship between non-normalized shape similarity Euclidean distances (X-axis) and the resultant normalized values (Y-axis), for the data points shown in FIG. 3A and FIG. 3B. The approximately linear relationship shown implies that the normalization does little to distort the population, although some bending is visible at the high-end (shape Euclidean distance values above 15).

FIG. 3C shows an approximately linear relationship between the majority of raw and normalized data point pairs, implying that the coefficient was a good choice for capturing the dynamic range of most of the dataset. The procedure was repeated for docking scores Y using α=0.25 (data not shown). This normalization procedure may allow for RepurposeVS to better predict viable drug-protein signatures in an absolute manner, where relativistic knowledge of other drugs in an experimental cohort is not necessary to quantify and establish binding signatures. Thus, resulting Z-scores can be pooled across all protein target systems for global objective prioritization of drug-target predictions.

E. Drug Shape Deviation Score

To determine shape similarity for drugs shared between unique protein target pairs, the "Drug Shape Deviation Score" ($\overline{F}$) metric was created. For analysis, target pairs should have at least three drugs predicted in common (i.e. within top 40 ranking for each protein target via Z-score). A "permutation of differences" (Equations (9)-(12)) approach was applied to arrive at a score within the 0-1 unit range that reflects the average shape deviation of the predicted common drugs for a protein target pair. The process may be as follows:

$$V = \{v_1, v_2, \ldots, v_n\} \quad (9)$$

where, for a given protein target pair, V is the set of common drugs, $$F = \{f_k = |a_{k_1} - a_{k_1}| \,|\, a_k = [v_i, v_j] \in C_2(V)\} \quad (10)$$

$$|F| = \binom{n}{2} = \frac{(n-1)n}{n} \quad (11)$$

$$\overline{F} = \sum_{k=1}^{|F|} \frac{f_k}{|k|} \quad (12)$$

$a_k$ is the Euclidean distance between a pair of common drugs, $C_2(V)$ is the set of all combinations of two elements from V without replacement to generate the number of difference values, F is the set of differences between the Euclidean distances via all possible permutations, |F| is the number of elements within set F, and $\overline{F}$ is the average across all Euclidean distance values.

F. Kinase Binding Assay

Kinase assays were performed using Kinomescan, by Discoverx, CA, USA and Caliper LabChip 3000 by Caliper Life sciences, USA as described previously. The determination of MBZ thermodynamic binding affinities ($K_d$) to kinase targets predicted by RepurposeVS was performed by using active site-directed competition binding. Kinase-tagged T7 phage strains were grown in parallel in 24-well blocks in an E. coli host derived from the BL21 strain. E. coli bacteria were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μm sieves) to remove cell debris. The remaining kinases were produced in HEK-293 cells and subsequently tagged with DNA for qPCR detection. Streptavidin-coated magnetic beads were treated with control (biotinylated) for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, control liganded affinity beads, and mebendazole in 1× binding buffer (20% SeaBlock, 0.17×PBS, 0.05% Tween 20, 6 mM DTT). Mebendazole was prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (lx PBS, 0.05% Tween 20). The beads were then re-suspended in elution buffer (1×PBS, 0.05 Tween 20, 0.5 μM non-biotinylated affinity ligand) and incubated at room temperature with shaking for 30 minutes. The kinase concentration in the eluates was measured by qPCR. Drugs that bind the kinase active site and directly prevent kinase binding to the immobilized ligand may reduce the amount of kinase captured, whereas drugs that do not bind the kinase have no effect on the amount of kinase captured. The amount of kinase captured in test versus control samples were measured by using a quantitative, precise and ultra-sensitive qPCR method that detects the associated DNA label. Using (13), the primary screen binding interactions are reported as '% Ctrl' (Percent kinase remaining activity), where lower numbers indicate stronger hits.

$$\text{Percent Control (\% Ctrl)} = \frac{\text{Mebendazole signal} - \text{Positive control signal}}{\text{DMSO Negative control signal} - \text{Positive control signal}} \times 100 \quad (13)$$

In a similar manner, binding constants ($K_d$) for mebendazole-kinase interactions are calculated by measuring the amount of kinase captured as a function of the mebendazole concentration in a dose response manner. An 11-point 3-fold serial dilution of each test compound was prepared in 100% DMSO at 100× final test concentration and subsequently diluted to 1× in the assay (final DMSO concentration=1%). Most $K_d$s were determined using a starting concentration=30,000 nM. If the initial $K_d$ determined was <0.5 nM (the lowest concentration tested), the measurement was repeated with a serial dilution starting at a lower starting concentration. Binding constants ($K_d$) were calculated with a standard dose-response curve (drug dose (x-axis)–qPCR signal (y-axis)) using the Hill equation in (14) with the Hill Slope set to −1.

$$\text{Response}(Y) = \text{Background} + \frac{\text{Signal(max)} - \text{Background}}{1 + \left(\frac{k_d}{\text{Drug Dose }(X)}\right)^{\text{Hill Slope}}} \quad (14)$$

G. Repurposing Potential

Original drug class indications, obtained from DrugBank, were given a "Repurposing Potential Score" (T) based on the number of drugs studied for a given approved indication class and the number of unique RepurposeVS-predicted disease classes for that indication class. Equation (15) represents the repurposing potential score (T) for a given disease class i:

$$T = \frac{d_i}{d_{neo}} + \frac{k_i}{k_{neo}} \quad (15)$$

where $d_i$ and $d_{neo}$ correspond the number of drugs approved for disease classes "i" and neoplasms, respectively, and $k_i$ and $k_{neo}$ correspond to the number of predicted new disease classes excluding the original for disease classes "i" and neoplasms. All disease classes are normalized to the neoplastic disease class since it contained both the greatest number of drugs with unique indications and predicted new diseases classes. The Online Mendelian Inheritance in Man (OMIM) and the Comparative Toxicogenomics Database (CTD) were used to annotate disease classes for predicted drug-protein target interactions.

II. Virtual Screening Performance

Virtual screenings were performed on a set of 12 pharmaceutically relevant protein targets to assess the accuracy of RepurposeVS. RepurposeVS performed superiorly to GLIDE, a docking algorithm found to be accurate in high-throughput virtual screenings, in enriching for known drug binders to a protein target over a set of 3,671 drugs (FIG. 4A and FIG. 4B).

Figure 4A:
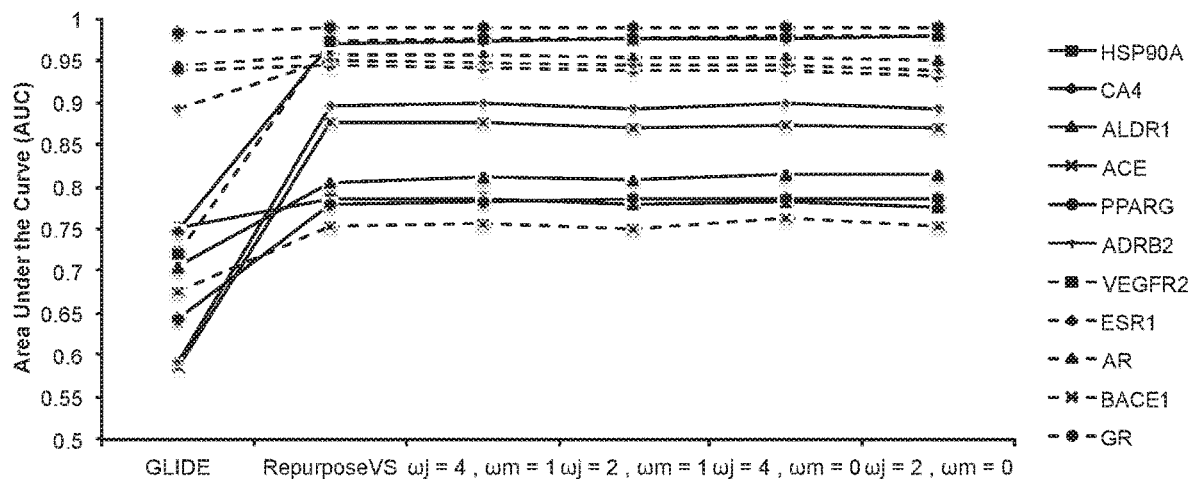
FIGS. 4A and 4B show performance of methods compared to conventional methods according to embodiments of the present technology.
Figure 4B:
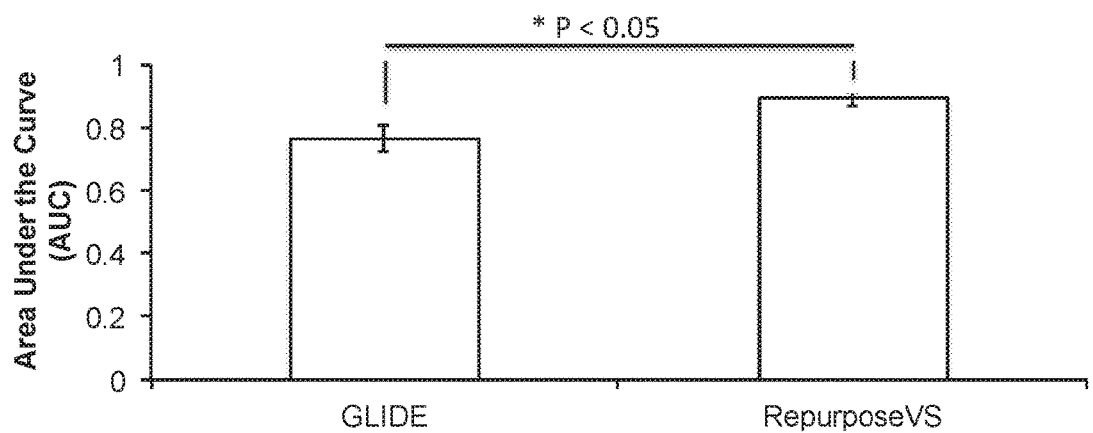

FIGS. 4A and 4B show areas under the curve (AUCs) for virtual screening of approved active drugs across 12 protein targets. FIG. 4A shows outcomes of GLIDE docking and RepurposeVS in virtual screening experiments enriching for true active drugs for a subset of the noted protein targets. The remaining conditions reflect adjusted weights for the docking parameter ($\omega_j$) and protein shape parameter ($\omega_m$) in RepurposeVS (Eq. 1). FIG. 4B shows average AUC across all 12 targets for each method. In FIG. 4B, the average AUC for GLIDE is 0.765, and the average AUC for RepurposeVS is 0.890. A method not shown in FIG. 4B similar to RepurposeVS but without an atom pair score and without rigorous normalization has an average AUC of 0.860.

Figure 5:
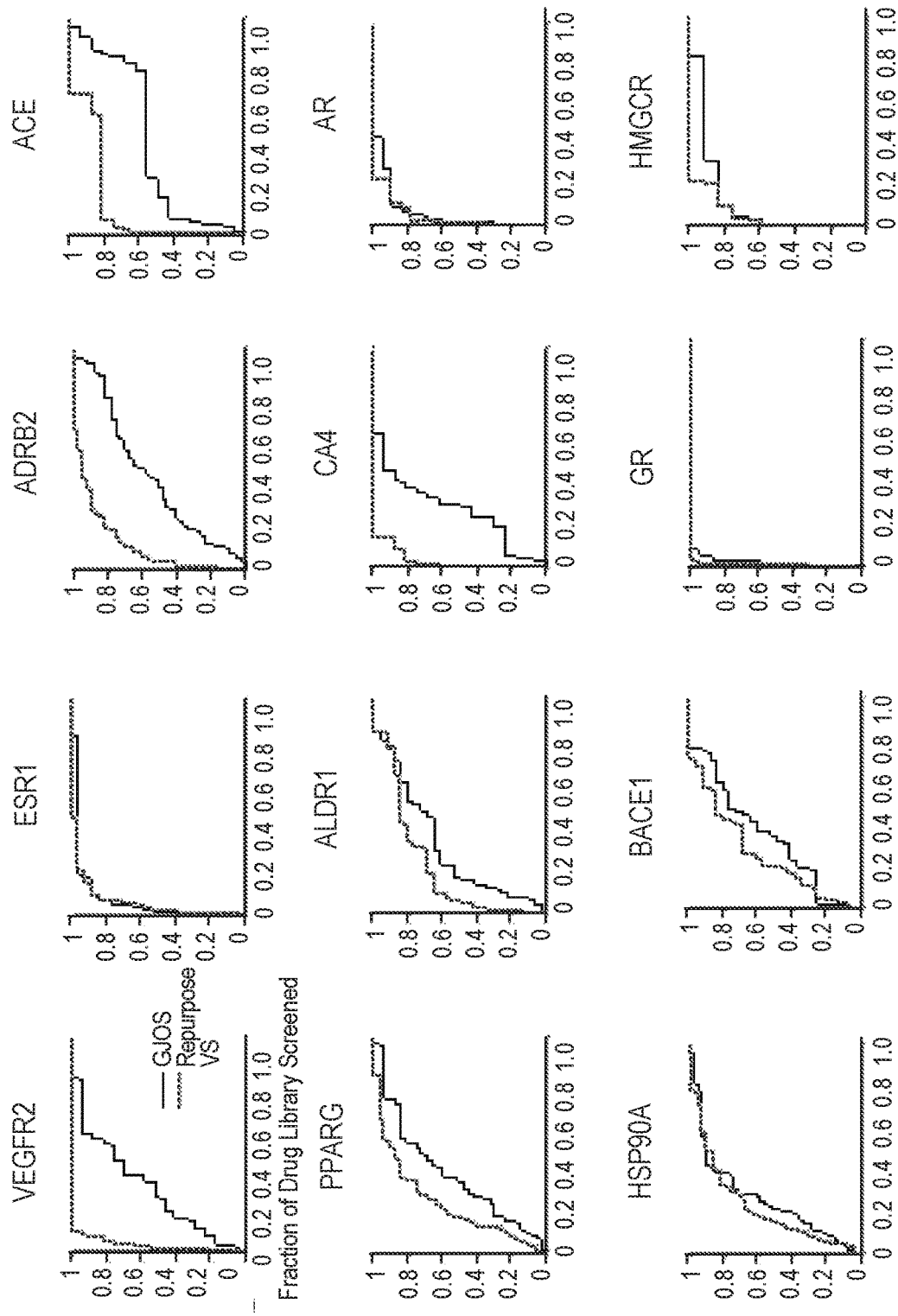
FIG. 5 shows receiver operating curves of virtual screening outcomes according to embodiments of the present technology.

Using a paired, one-tailed student's t-test, RepurposeVS performed statistically significantly better than GLIDE ($p<0.01$). Receiver operating curves demonstrate that RepurposeVS increased accuracy the most for solvent-exposed binding pockets, such as VEGFR2 kinase domain and $\beta_2$-adrenergic G protein-coupled receptor, whereas minimal increase occurred for buried pockets such as the estrogen and androgen nuclear receptors (FIG. 5). FIG. 5 shows receiver operating curves (ROCs) of virtual screening outcomes for GLIDE docking and RepurposeVS methods applied to 12 protein targets for benchmarking. ROCs were used to calculate areas under the curve (AUCs) in FIGS. 4A and 4B.

This differential may be attributed to greater flexibility in binding pose in exposed sites, which are specifically reflected by the docking score and pocket shape terms. Altering the weights $\omega_k$ and $\omega_m$ for docking score and pocket shape, respectively, had no appreciable effect on performance (FIG. 4A). This suggests that the other parameters in compensate for the imprecision derived from the nature of exposed pockets and that RepurposeVS is a robust method applicable to diverse protein targets.

Figure 6A:
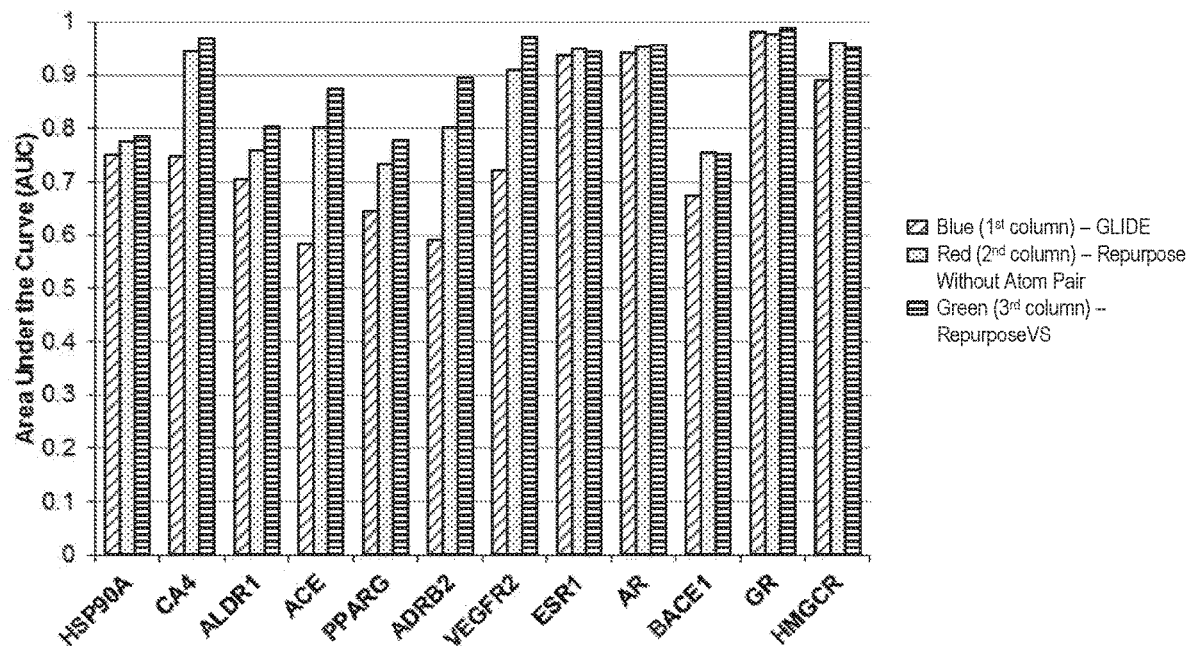
FIGS. 6A and 6B show performance of methods compared to conventional methods according to embodiments of the present technology.
Figure 6B:
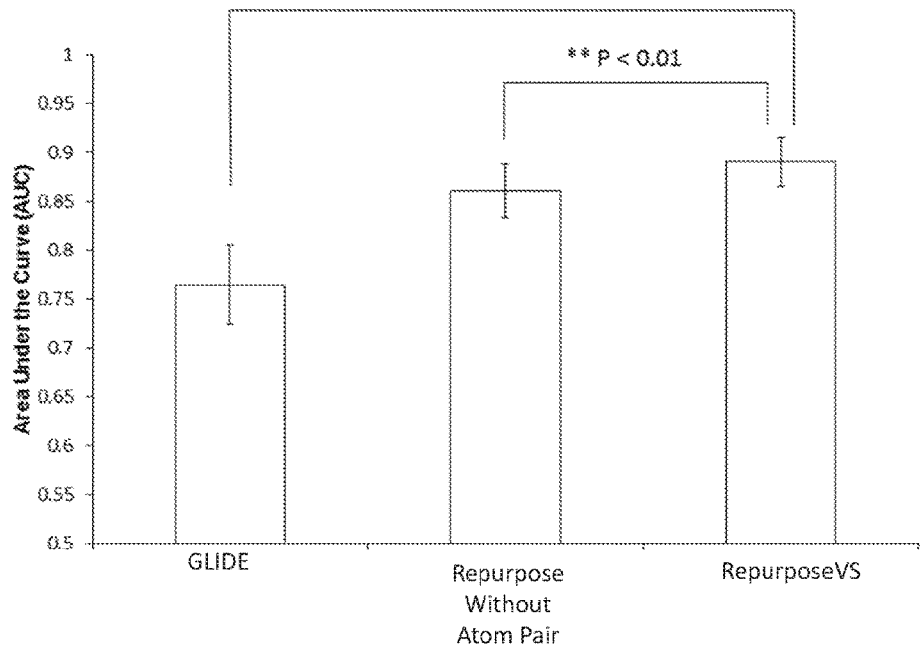

Similar to FIGS. 4A and 4B, FIGS. 6A and 6B show AUCs for virtual screening of approved active drugs across 12 protein targets. FIG. 6A shows outcomes of GLIDE docking, an interaction score without the atom pair score and without rigorous normalization ("Repurpose without atom pair"), and RepurposeVS in the first, second, and third columns, respectively, for each protein target. FIG. 6B shows average AUC across all 12 targets for each method. FIG. 6B shows the average AUC for GLIDE is 0.765, the average AUC for Repurpose without atom pair is 0.860, and the average AUC for RepurposeVS is 0.890. Using a paired, one-tailed student's t-test, RepurposeVS performed statistically significantly better than GLIDE and Repurpose without atom pair ($p<0.01$).

III. Global Validation Using Shape Similarity

RepurposeVS was applied to a set of 2,335 human protein target crystal structures and globally validated using the concept of similarly shaped drugs binding to protein target sites of similar shape. Shape complementarity may be a critical aspect of biomolecular recognition, though it may not explain all possible binding modes. Nonetheless, it has generally been noted that drugs that interact with protein binding sites of similar shapes tend to exhibit shape similarity to each other. We first determined that the notion of similarly shaped drugs bind to similar protein pockets is upheld using the reference co-crystallized molecules for the protein target set.

Figure 7A:
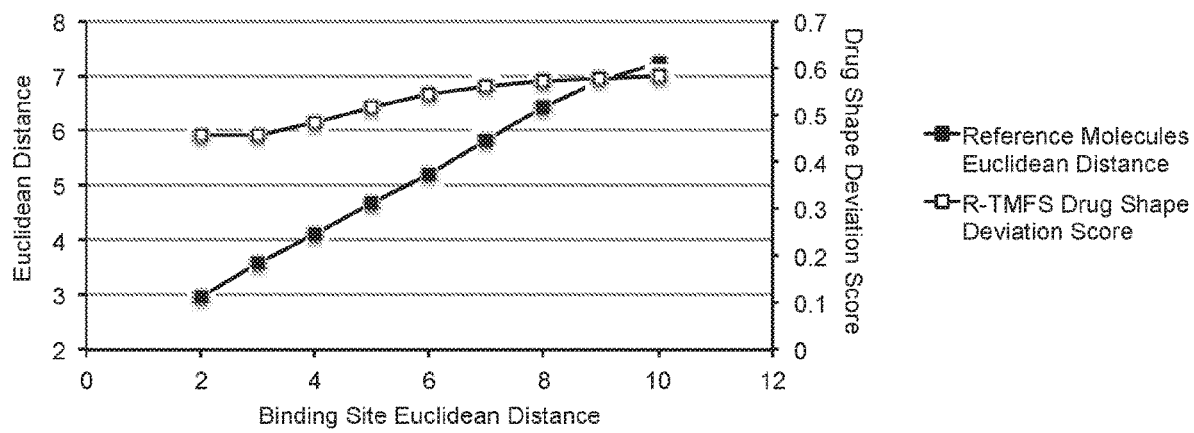
FIGS. 7A and 7B show trends in drug shape as a function of binding site shape and structural differences between protein target pairs according to embodiments of the present technology.
Figure 7B:
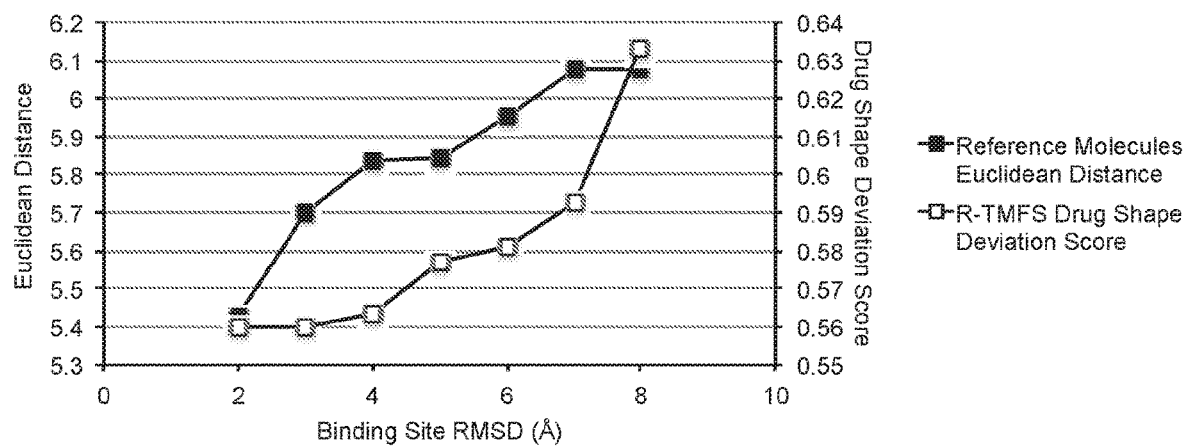

Similarity between protein target pockets was quantified using two metrics: (1) Euclidean distance of the space-filling protomol structure (FIG. 7A), and (2) root-mean-square deviation (RMSD) of binding site residues 6 Å from the geometric center of the bound molecule (FIG. 7B). The former metric characterizes the binding site occupancy volume whereas the latter metric is a topological term reflective of the binding site Cα backbone. RMSD values were calculated using Maestro. Line plots depicting shape Euclidean distances between co-crystallized reference molecules and normalized "Drug Shape Deviation Scores" ($\bar{F}$) against (FIG. 7A) binding pocket shape differences quantified by Euclidean distances and (FIG. 7B) backbone root-mean-squared deviation (RMSD) in angstroms. The data was binned into 1-unit groups with their means represented in the plot. Smaller Euclidean distances or RMSDs imply greater similarity. There exists a direct correlation between drug-drug shape Euclidean distances and protein-protein binding site shape Euclidean distances (FIG. 7A) and backbone RMSDs (FIG. 7B).

This implies that for true biochemical associations, determined via crystal structures, similarly shaped molecules bind protein pockets of similar shape and topology. Using the "Drug Shape Deviation Score", $\bar{F}$ (12), a similar trend was observed for drugs predicted by RepurposeVS (top 40 by Z-score) to bind the same protein targets. Thus, RepurposeVS may be a valid method for determining drug-target associations across a large and diverse protein target set via the pharmacological metric of similarly shaped drugs binding similarly shaped protein pockets.

IV. In Vitro Biological Validation Using Mebendazole for Cancer Drug Repurposing To biologically confirm RepurposeVS predictions in vitro, we tested the binding of protein kinase target hits to mebendazole (MBZ) for cancer drug repurposing. MBZ was originally approved for its potent nanomolar inhibition of hookworm tubulin. It is thought that its cross-over effect on mammalian tubulin, though with 1000× less potency, is responsible for its anti-cancer efficacy in vitro. Using kinase binding assays, nano- and micromolar inhibition of several predicted kinase targets of MBZ was confirmed.

Figure 8:
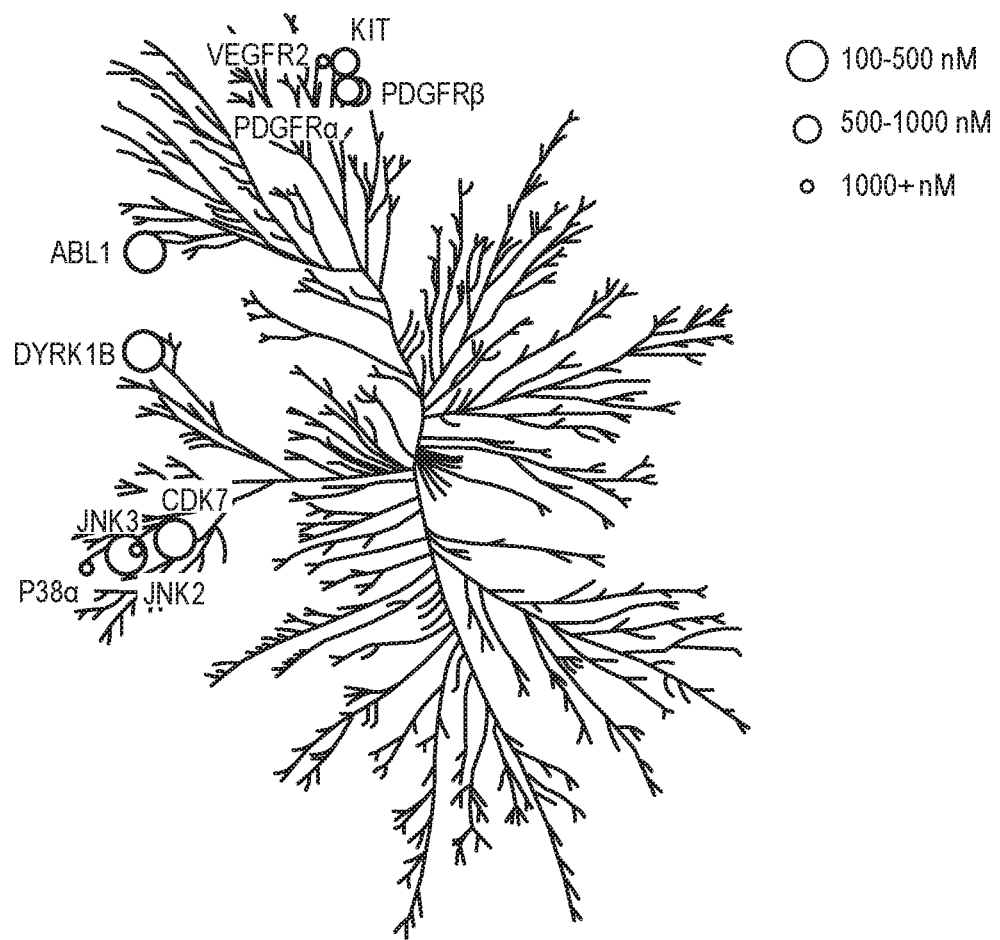
FIG. 8 shows predicted mebendazole kinase targets according to embodiments of the present technology.

FIG. 8 shows validated mebendazole (MBZ) kinase targets predicted from RepurposeVS. Kinases for which binding affinities were determined are shown on the kinome phylogenetic tree.

MBZ appears to inhibit kinases found within two main branches of the kinome phylogenetic tree, with nanomolar potency clustering on one branch and micromolar potency on the other (FIG. 8). However, intra-branch variability in potency is also observed. It is likely that the semi-promiscuous nature of MBZ (FIG. 8) towards kinases is a result of a small fragment that allows it to interact with the benzimidazole moiety acting as head group anchor connecting loop residues between the c-lobe and n-lobe. MBZ is also dually able to form water-mediated contacts or directly interact with ATP site cavity-forming residues in the absence of water molecules. Our predicted kinase hits and the activity data of MBZ indicate that its anti-cancer properties may be due to a synergistic inhibition of tubulin as well as kinase activity. Interestingly, for lung cancer, combined inhibition of microtubules and DYRK1B, a MBZ target (Table 1), is a more potent therapeutic strategy than microtubule inhibitors alone. In this instance, a single drug such as MBZ, which has both properties, would be advantageous. RepurposeVS, thus, may be able to reliably predict targets for MBZ that contribute to its repurposing for cancers.

TABLE 1

Binding affinities of MBZ for predicted kinase hits.

| Kinase Target | Percent Control at 10 μM | Binding Affinity ($K_d$) in nM |
|---|---|---|
| ABL1(E255K)-phosphorylated | 2.2 | N/D |
| ABL1(T315I)-phosphorylated | 3.2 | N/D |
| ABL1-nonphosphorylated | 2 | N/D |
| ABL1-phosphorylated | 0.9 | 120 |
| CDK7 | 11 | 390 |
| CSNK1D | 36 | N/D |
| DYRK1A | 34 | N/D |
| DYRK1B | 5.6 | 340 |
| GSK3B | 35 | N/D |
| JAK3 | 29 | N/D |
| JNK1 | 14 | N/D |
| JNK2 | 9.6 | 1090 |
| JNK3 | 3 | 410 |
| KIT (D816V) | 7.4 (33) | 750 |
| MET | 32 | N/D |
| P38-alpha | 17 | 1660 |
| PDGFR-A | 7.8 | 820 |
| PDGFR-B | 3.2 | 660 |
| PIK3CG | 18 | N/D |
| SRC | 34 | N/D |
| ULK2 | 30 | N/D |
| VEGFR-2 | 30 | 3600 |

V. Drug Repurposing Potential

Figure 9:
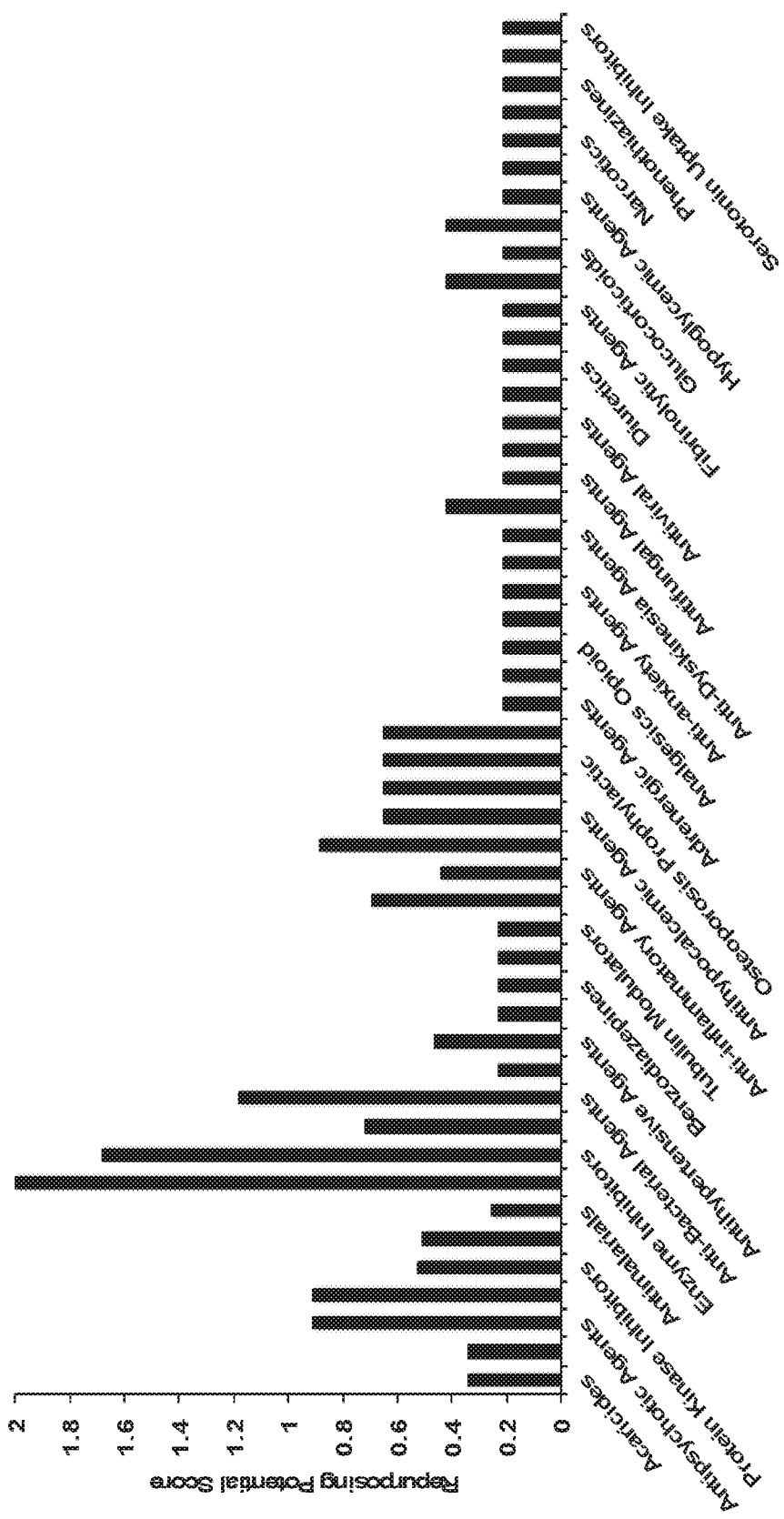
FIG. 9 shows predicted repurposing potentials according to embodiments of the present technology.

RepurposeVS was used to provide a cursory assessment the potential repurposing space for FDA approved drugs based on their drug classes (FIG. 9). We devised a repurposing potential score (7) in Equation (15) for this purpose. Anti-neoplastic agents are shown to have the greatest repurposing potential with regards to the number of drugs and the diversity of newly predicted disease categories, with a total of 47 drugs and 8 disease categories. The nutritional-metabolic and neoplasm disease classes are also predicted to have the greatest number of drugs with the greatest number of unique original indications repurposed to them with 143 drugs/29 indications and 123 drugs/22 indications, respectively.

The overrepresentation of anti-neoplastic drugs is expected as tumor development is due to perturbations in a variety of cell processes that are likely shared with other diseases. Dysregulated kinase signaling, for example, is a ubiquitous pathogenic disease mechanism given the role of kinases in signal transduction. Thus, kinase inhibitors would be expected to potentially be useful in other diseases. In addition, some cancer drugs exhibit polypharmacology that simultaneously alter multiple cell processes. Alternatively, anti-infection agents may exhibit relatively low repurposing potential (FIG. 9).

This emphasizes the selectivity of these agents towards non-human targets for efficacy and desired therapeutic indices. Some of these drugs, however, exhibit modest repurposing potential. These include anti-bacterial agents, possibly attributed to structural similarity between bacterial motifs and human proteins. Antipsychotic agents and other psychiatry-approved drugs also are predicted to have modest repurposing potential. These drugs typically exhibit polypharmacology through GPCR-mediated interactions, and some are being repurposed for cancer therapy. The outcomes of the potential drug repurposing space are in pharmacological and clinical agreement with the known properties of the mentioned drugs, further confirming the ability of RepurposeVS to empirically predict drug-target signatures for higher-order pharmacologic assessment.

RepurposeVS is a combined drug-centric and protein-centric computational method for formulating drug-target signature predictions in drug repurposing. Validity was confirmed through benchmark virtual screenings using 12 protein targets of pharmaceutical interest to better enrich for their respective known approved drugs over GLIDE docking. RepurposeVS was also validated by recapitulating that drugs of similar shapes were predicted to bind similarly shaped protein pockets when defining pocket shapes through drug occupancy, and also by confirming predicted kinase hits of mebendazole via kinase binding assays. Finally, RepurposeVS was used to quantify "repurposing potential scores" for drugs categorized by disease indication and showed that anti-infection compounds had the least repurposing potential whereas anti-neoplastic drugs had the greatest. One limitation, however, is that diverse binding modes and protein flexibility are not accounted for. However, RepurposeVS aims only to reestablish the experimental binding states obtained from crystallography so as to decrease false positive and false negative outcomes in virtual screenings. Overall, we believe RepurposeVS to be an efficient computational method to aid drug repurposing endeavors.

VI. Computer System

Figure 10:
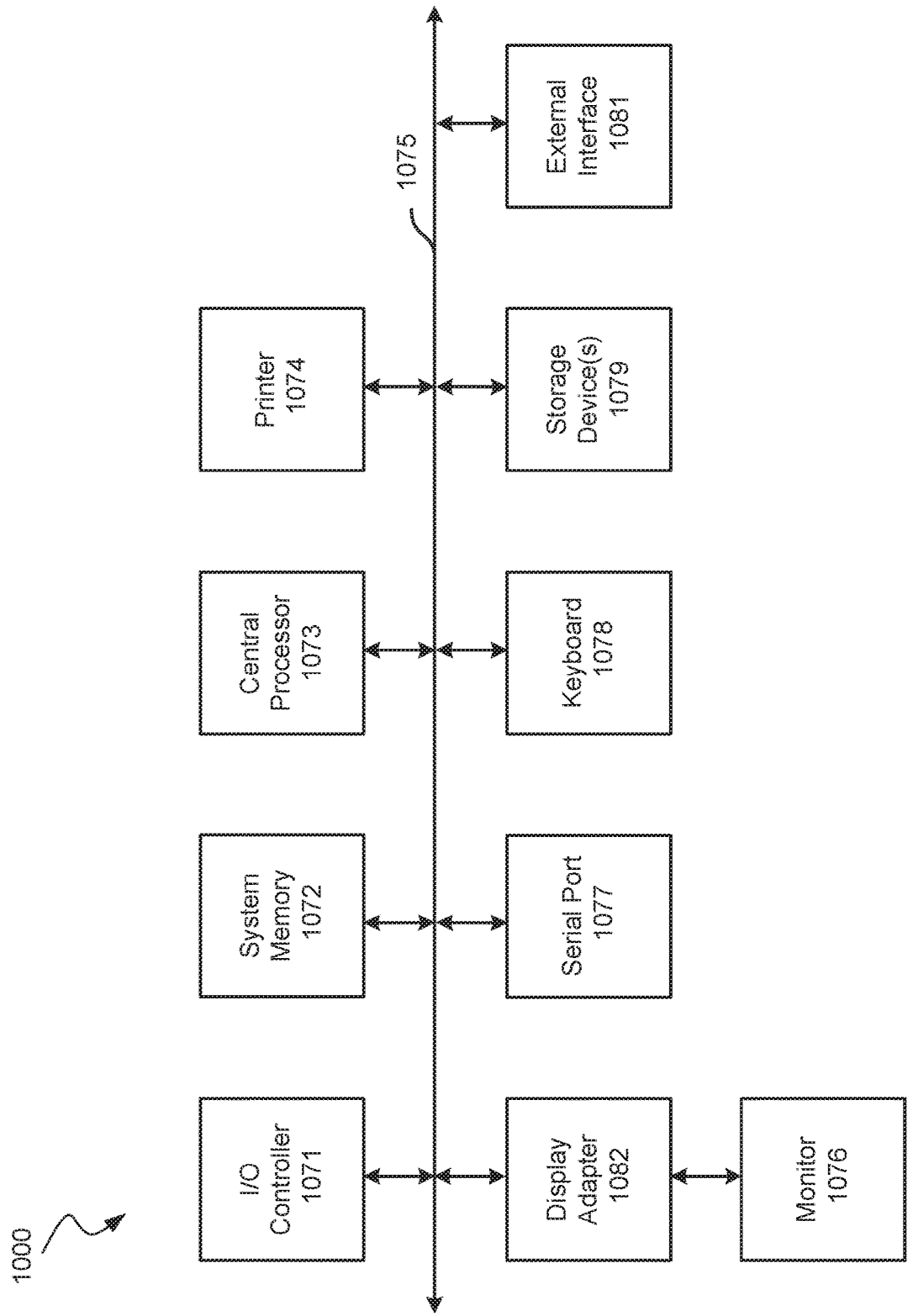
FIG. 10 shows a block diagram of an example computer system 1000 usable with systems and methods according to embodiments of the present technology.

Any of the computer systems mentioned herein may utilize any suitable number of subsystems. Examples of such subsystems are shown in FIG. 10 in computer apparatus 1000. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 10 are interconnected via a system bus 1075. Additional subsystems such as a printer 1074, keyboard 1078, storage device(s) 1079, monitor 1076, which is coupled to display adapter 1082, and others are shown. Peripherals and input/output (I/O) devices, which couple to I/O controller 1071, can be connected to the computer system by any number of means known in the art, such as serial port 1077. For example, serial port 1077 or external interface 1081 (e.g. Ethernet, Wi-Fi, etc.) can be used to connect computer system 1000 to a wide area network such as the Internet, a mouse input device, or a scanner. The interconnection via system bus 1075 allows the central processor 1073 to communicate with each subsystem and to control the execution of instructions from system memory 1072 or the storage device(s) 1079 (e.g., a fixed disk, such as a hard drive or optical disk), as well as the exchange of information between subsystems. The system memory 1072 and/or the storage device(s) 1079 may embody a computer readable medium. Any of the data mentioned herein can be output from one component to another component and can be output to the user.

A computer system can include a plurality of the same components or subsystems, e.g., connected together by external interface 1081 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++, Python, or Perl using, for example, conventional or object oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method for identifying protein-drug interactions, the method comprising:

receiving test ligand molecular data corresponding to a test ligand that is a candidate drug;

receiving protein molecular data corresponding to a protein;

receiving reference ligand data corresponding to a reference ligand that binds to the protein;

generating, by a computer system, an atom pair score from an atom descriptor of the test ligand and a corresponding atom descriptor of the reference ligand;

calculating an interaction score, the interaction score including a sum comprising the atom pair score;

normalizing the interaction score using a normalization weight calculated using the formula $N_\alpha=1-|1-S_\alpha(x)|$, wherein x is a raw parameter, S(x) is a sigmoid function, and a is a tunable scalar coefficient chosen to maximize an information-preserving variance in an image of N(x);

validating, based on the interaction score exceeding a threshold value, a first interaction between the test ligand and the protein;

in response to validating the first interaction, performing an assay using the test ligand and the protein to obtain an assay result experimentally;

after validating the first interaction, receiving the assay result; and confirming the first interaction based at least on the received assay result.

2. The method of claim 1, further comprising:

calculating, by the computer system, a shape score including one or more shape contributions, each shape contribution corresponding to a respective shape descriptor, wherein a respective contribution includes a first part and a second part, the first part providing a first shape score from a first respective shape function of the protein and the test ligand corresponding to the respective shape descriptor, and the second part providing a second shape score from a second respective shape function of the reference ligand and the test ligand corresponding to the respective shape descriptor;

calculating, by the computer system, a total similarity score including one or more similarity contributions, each similarity contribution corresponding to a respective similarity descriptor, wherein a respective similarity contribution provides a respective similarity score between a respective similarity function of the test ligand and the respective similarity function of the reference ligand;

calculating, by the computer system, a correction score, the correction score being a difference between a first sum and a second sum, the first sum being of energies of contact points between the reference ligand and the protein; and adding the shape score, the similarity score, and the correction score to the interaction score.

3. The method of claim 2, further comprising:

calculating a docking score between the test ligand and the protein; and adding the docking score to the interaction score.

4. The method of claim 3, further comprising:

normalizing the interaction score using weights for the atom pair score, the first respective shape functions, the second respective shape functions, and the docking score.

5. The method of claim 3, wherein the interaction score Z for a qth test ligand, a pth protein, and a rth reference ligand is calculated using the formula:

$$Z(q, p, r) = \omega_j Y(p, q) + \omega_k P(r, q) + \sum_{m=1}^{M}[\omega_m f_m(p, q) + \omega'_m f'_m(r, qp, q)] + \sum_{n=1}^{N} X_n(r, q) + CS(OLIC).$$

6. The method of claim 2, wherein the one or more shape contributions include a Euclidean distance metric.

7. The method of claim 2, wherein the one or more similarity contributions include at least one of: a number of H-bond acceptors, number of H-bond donors, dipole, electron affinity, globularity, molecular weight, ClogP, number of rotatable bonds, solvent-accessible surface area, and volume.

8. The method of claim 2, wherein:

the first sum of the correction score for a pth protein is computed as: $S(OLIC-r)_p = \sum_{n=1}^{NR} \omega_n E_{n,p}$, where NR is a number of contact points between the reference ligand and the protein, $\omega_n$ is a weighting factor for the nth contact point, and $E_{n,p}$ is an energy associated with the nth contact point.

9. The method of claim 2, wherein:

the second sum of the correction score for a qth test ligand and a pth protein is computed as: $S(OLIC-q)_p = \sum_{n=1}^{NQ} \omega_n E_{n,q,p}$, where NQ is a number of contact points between the test ligand and the protein, $\omega_n$ is a weighting factor for the nth contact point, and $E_{n,p,q}$ is an energy associated with the nth contact point.

10. The method of claim 1, wherein a portion of the reference ligand data is extracted from a known structure of a complex of the protein bound to the reference ligand.

11. The method of claim 1, wherein calculating the atom pair score includes a similarity Tanimoto coefficient.

12. A computer product comprising a non-transitory computer readable medium storing a plurality of instructions for controlling a computer system to perform the method of claim 1.

13. A system comprising:
the computer product of claim 12; and
one or more processors for executing instructions stored on the computer readable medium.

14. The method of claim 1, wherein the assay comprises a kinase assay.

15. The method of claim 1, wherein:
the test ligand is a first test ligand, and
the method further comprises:
calculating interaction scores for 39 additional test ligands in the same manner as for the first test ligand.

16. The method of claim 1, wherein the threshold value is a score value.

17. The method of claim 1, further comprising:
determining a plurality of interaction scores for a plurality of test ligands and protein combinations;
ranking the plurality of interaction scores; and
using a ranking as the threshold value.

* * * * *

UNITED STATES PATENT AND TRADEMARK OFFICE
CERTIFICATE OF CORRECTION

PATENT NO. : 10,916,331 B2
APPLICATION NO. : 15/577719
DATED : February 9, 2021
INVENTOR(S) : Sivanesan Dakshanamurthy et al.

It is certified that error appears in the above-identified patent and that said Letters Patent is hereby corrected as shown below:

In the Specification

In Column 1, Lines 15-24, delete "STATEMENT AS TO RIGHTS TO INVENTIONS MADE UNDER FEDERALLY SPONSORED RESEARCH AND DEVELOPMENT
This invention was made with U.S. government support under grant numbers BC062416, BC096277 (SB, SD), R01 CA 170653 (SB, SD), awarded by the Department of Defense; and under grant number NIH-P30 CA51008, awarded by the National Institutes of Health. The government has certain rights in the invention." and Insert -- STATEMENT REGARDING FEDERALLY FUNDED RESEARCH
This invention was made with government support under grant numbers CA051008, CA170653 awarded by the National Institutes of Health. The government has certain rights in the invention. --.

Signed and Sealed this
Second Day of January, 2024

Katherine Kelly Vidal
*Director of the United States Patent and Trademark Office*